US012679850B2

(12) United States Patent
Jin et al.

(10) Patent No.: US 12,679,850 B2
(45) Date of Patent: Jul. 14, 2026

(54) TYK2 INHIBITORS AND USES THEREOF

(71) Applicant: Alumis Inc., South San Francisco, CA (US)

(72) Inventors: Bohan Jin, South San Francisco, CA (US); Qing Dong, South San Francisco, CA (US); Gene Hung, South San Francisco, CA (US)

(73) Assignee: Alumis Inc., South San Francisco, CA (US)

( * ) Notice: Subject to any disclaimer, the term of this patent is extended or adjusted under 35 U.S.C. 154(b) by 380 days.

(21) Appl. No.: 18/026,309

(22) PCT Filed: Sep. 16, 2021

(86) PCT No.: PCT/US2021/050649
§ 371 (c)(1),
(2) Date: Mar. 14, 2023

(87) PCT Pub. No.: WO2022/060973
PCT Pub. Date: Mar. 24, 2022

(65) Prior Publication Data

US 2023/0357273 A1 Nov. 9, 2023

Related U.S. Application Data

(60) Provisional application No. 63/079,217, filed on Sep. 16, 2020.

(51) Int. Cl.

| | |
|---|---|
| ***C07D 487/22*** | (2006.01) |
| ***A61K 31/5025*** | (2006.01) |
| ***A61K 31/519*** | (2006.01) |
| ***A61P 37/02*** | (2006.01) |
| ***C07D 498/22*** | (2006.01) |

(52) U.S. Cl.
CPC .................................. *C07D 498/22* (2013.01)

(58) Field of Classification Search
CPC C07D 487/22; C07D 498/22; A61K 31/5025; A61K 31/519; A61P 37/02
See application file for complete search history.

(56) References Cited

U.S. PATENT DOCUMENTS

| | | | |
|---|---|---|---|
| 8,933,084 | B2 | 1/2015 | Andrews et al. |
| 9,096,609 | B2 | 8/2015 | Hoflack et al. |
| 9,370,520 | B2 | 6/2016 | Hoflack et al. |
| 9,493,476 | B2 | 11/2016 | Andrews et al. |
| 9,714,258 | B2 | 7/2017 | Cui et al. |
| 9,718,822 | B2 | 8/2017 | Andrews et al. |
| 9,750,744 | B2 | 9/2017 | Andrews et al. |
| 9,840,519 | B2 | 12/2017 | Andrews et al. |
| 9,902,741 | B2 | 2/2018 | Andrews et al. |
| 10,180,422 | B1 | 1/2019 | Sigal |
| 10,246,466 | B2 | 4/2019 | Cui et al. |
| 10,294,242 | B2 | 5/2019 | Cui et al. |
| 10,316,044 | B2 | 6/2019 | Cui et al. |
| 10,370,727 | B2 | 8/2019 | Nanda et al. |
| 10,378,068 | B2 | 8/2019 | Nanda et al. |
| 10,618,912 | B2 | 4/2020 | Cui et al. |
| 10,647,730 | B2 | 5/2020 | Andrews et al. |
| 10,655,186 | B2 | 5/2020 | Nanda et al. |
| 10,688,100 | B2 | 6/2020 | Andrews et al. |
| 10,689,400 | B2 | 6/2020 | Cui et al. |
| 10,724,102 | B2 | 7/2020 | Nanda et al. |
| 10,745,416 | B2 | 8/2020 | Rogers et al. |
| 10,907,215 | B2 | 2/2021 | Nanda et al. |
| 11,053,219 | B2 | 7/2021 | Jin et al. |
| 2011/0230467 | A1 | 9/2011 | Shirakami et al. |

(Continued)

FOREIGN PATENT DOCUMENTS

| | | | |
|---|---|---|---|
| CN | 104884454 | A | 9/2015 |
| CN | 105111151 | A | 12/2015 |

(Continued)

OTHER PUBLICATIONS

International Preliminary Report on Patentability for International Patent Application No. PCT/US2021/050649, mailed Mar. 30, 2023.

Xu, S., et al., "Design, synthesis and biological evaluation of new molecules inhibi ting epidermal growth factor recep tor threonine 790–––+methionine 790 mutant", Med. Chem. Commun., 3:1155-1159, (2012).

Coffey, G., et al., "Specific Inhibition of Spleen Tyrosine Kinase Suppresses Leukocyte Immune Function and Inflammation in Animal Models of Rheumatoid Arthritis", The Journal of Pharmacology and Experimen tal Therapeu tics, 340(2):350-359, (2012).

(Continued)

*Primary Examiner* — Brenda L Coleman
(74) *Attorney, Agent, or Firm* — Goodwin Procter LLP

(57) ABSTRACT

Described herein are compounds of Formula (I) that are useful in treating a TYK2-mediated disorder. In some embodiments, the TYK2-mediated disorder is an autoimmune disorder, an inflammatory disorder, a proliferative disorder, an endocrine disorder, a neurological disorder, or a disorder associated with transplantation.

Formula (I)

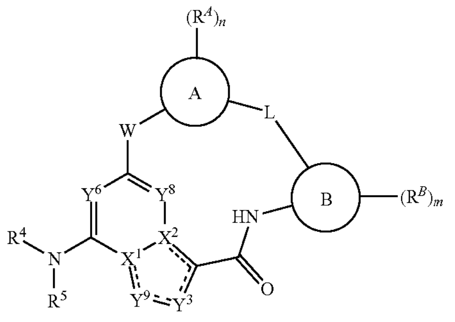

17 Claims, No Drawings

(56) References Cited

U.S. PATENT DOCUMENTS

| | | | |
|---|---|---|---|
| 2015/0299214 A1 | 10/2015 | Uchida et al. | |
| 2016/0024114 A1 | 1/2016 | Blom et al. | |
| 2016/0207883 A1 | 7/2016 | Shirahase et al. | |
| 2017/0338422 A1 | 11/2017 | Wang et al. | |
| 2018/0325901 A1 | 11/2018 | Cui et al. | |
| 2019/0247398 A1 | 8/2019 | Zhao et al. | |
| 2019/0381048 A1 | 12/2019 | Cui et al. | |
| 2020/0123166 A1 | 4/2020 | Bryan et al. | |
| 2020/0157119 A1 | 5/2020 | Cui et al. | |
| 2020/0190199 A1 | 6/2020 | Chuang et al. | |
| 2020/0216451 A1 | 7/2020 | Zhao et al. | |
| 2020/0291042 A1 | 9/2020 | Dai et al. | |
| 2020/0330452 A1 | 10/2020 | Rickard et al. | |
| 2020/0385386 A1 | 12/2020 | Wu et al. | |
| 2020/0405725 A1 | 12/2020 | Wang et al. | |
| 2021/0000830 A1 | 1/2021 | Kozaki et al. | |
| 2021/0023086 A1 | 1/2021 | Bilenker et al. | |
| 2021/0047330 A1 | 2/2021 | Wang et al. | |
| 2022/0235035 A1 | 7/2022 | Jin et al. | |
| 2023/0021554 A1 | 1/2023 | Jin et al. | |
| 2025/0188093 A1* | 6/2025 | Brameld .............. | C07D 487/22 |

FOREIGN PATENT DOCUMENTS

| | | | |
|---|---|---|---|
| CN | 107735399 | A | 2/2018 |
| CN | 113874021 | A | 12/2021 |
| EP | 2361902 | A1 | 8/2011 |
| EP | 2428508 | A1 | 3/2012 |
| EP | 3040329 | A1 | 7/2016 |
| EP | 3607944 | A1 | 2/2020 |
| JP | 2010503690 | A | 2/2010 |
| JP | 2016-506369 | A | 3/2016 |
| JP | 2017-512749 | A | 5/2017 |
| RU | 2005106871 | A | 10/2005 |
| WO | 200247690 | A1 | 6/2002 |
| WO | 2006105222 | A2 | 10/2006 |
| WO | 2009136995 | A2 | 11/2009 |
| WO | 2010058846 | A1 | 5/2010 |
| WO | 2012061418 | A2 | 5/2012 |
| WO | 2012061428 | A2 | 5/2012 |
| WO | 2012159557 | A1 | 11/2012 |
| WO | 2013001310 | A1 | 1/2013 |
| WO | 2013104573 | A1 | 7/2013 |
| WO | 2014074661 | A1 | 5/2014 |
| WO | 2015069310 | A1 | 5/2015 |
| WO | 2015084998 | A1 | 6/2015 |
| WO | 2015123453 | A1 | 8/2015 |
| WO | 2016196776 | A2 | 12/2016 |
| WO | 2017004342 | A1 | 1/2017 |
| WO | 2017087590 | A1 | 5/2017 |
| WO | 2017125534 | A1 | 7/2017 |
| WO | 2018067432 | A1 | 4/2018 |
| WO | 2018081417 | A2 | 5/2018 |
| WO | 2018165240 | A1 | 9/2018 |
| WO | 2018170381 | A1 | 9/2018 |
| WO | 2018186366 | A1 | 10/2018 |
| WO | 2019023417 | A1 | 1/2019 |
| WO | 202019376 | A1 | 1/2020 |
| WO | 2020086616 | A1 | 4/2020 |
| WO | 2020154474 | A1 | 7/2020 |
| WO | 2020156311 | A1 | 8/2020 |
| WO | 2020163778 | A1 | 8/2020 |
| WO | 2020185755 | A1 | 9/2020 |
| WO | 2020198379 | A1 | 10/2020 |
| WO | 2021092246 | A1 | 5/2021 |

OTHER PUBLICATIONS

Wrobleski, et al., "Highly Selective Inhibition of Tyrosine Kinase 2 (TYK2) for the Treatment of Autoimmune Diseases: Discovery of the Allosteric Inhibitor BMS-986165", J Med Chem 62(20):8973-8995 (2019).

Partial European Search Report for EP Patent Application No. 19877015.8, mailed Jun. 6, 2022.

International Search Report and Written Opinion for International Patent Application No. PCT/US2020/021850, mailed Jun. 24, 2020.

International Search Report and Written Opinion for International Patent Application No. PCT/US2019/057485, mailed Feb. 7, 2020.

International Search Report and Written Opinion for International Patent Application No. PCT/US2021/050649, mailed Dec. 6, 2021.

Office Action for Russian Patent Application No. 2021114368, mailed Feb. 28, 2022.

Jordan, V. C., "Tamoxifen: a most unlikely pioneering medicine", Nature Reviews: Drug Discovery, 2:205-213, (2003).

Vippagunta, S. R., et al., "Crystalline solids", Advanced Drug Delivery Reviews, 48(1):3-26, (2001).

Office Action for Saudi Patent Application No. 521421806, mailed Aug. 31, 2022.

Office Action for Singapore Patent Application No. 11202104017V, mailed Sep. 1, 2022.

Extended EP Search Report for European Patent Application No. 19877015.8, mailed Sep. 21, 2022.

Office Action for Chile Patent Application No. 202100989, mailed Oct. 17, 2022.

Extended EP Search Report for European Patent Application No. 20769748.3, mailed Dec. 22, 2022.

Office Action for Brazil Patent Application No. BR112021007679-4, mailed May 9, 2023.

Examination Report for Indian Patent Application No. 202117022424, mailed Nov. 29, 2022.

EP Examination Report for European Patent Application No. 19877015.8, mailed May 30, 2023.

First Examination Report for Indian Patent Application No. 202117041694, mailed May 8, 2023.

Office Action for Vietnam Patent Application No. 1-2021-02921, mailed Jul. 26, 2023.

Office Action for Japanese Patent Application No. 2021-523157, mailed Nov. 15, 2023.

Office Action for Chinese Patent Application No. 201980084885.9, mailed Dec. 27, 2023.

ACS. Registry Database, RN No. 42321-62-0 etc., Jun. 17, 2013.

Office Action for Chinese Patent Application No. 202080034800.9, mailed Nov. 29, 2023.

Office Action for Japanese Patent Application No. 2021-552136, mailed Feb. 16, 2024.

Zhe Nie, et al., "Structure-based design and synthesis of novel macrocyclic pyrazolo[1,5-a] [1,3,5]triazine compounds as potent inhibitors of protein kinase CK2 and their anticancer activities", Bioorganic & Medicinal Chemistry Letters, 18:619-623, (2008).

Office Action for Singapore Patent Application No. 11202104017V, mailed Jan. 10, 2024.

* cited by examiner

TYK2 INHIBITORS AND USES THEREOF

RELATED APPLICATIONS

This application is a national phase filing under 35 U.S.C. § 371 of International PCT) Patent Application No. PCT/US2021/050649, filed Sep. 16, 2021, which claims the benefit of U.S. Provisional Application No. 63/079,217, filed Sep. 16, 2020. The contents of each of which are incorporated herein by reference in their entireties.

FIELD OF THE INVENTION

Described herein are compounds, methods of making such compounds, pharmaceutical compositions and medicaments comprising such compounds, and methods of using such compounds for inhibiting nonreceptor tyrosine-protein kinase 2 ("TYK2"), also known as Tyrosine kinase 2.

BACKGROUND OF THE INVENTION

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFNζ (also known as limitin), and interleukins (e.g. IL-4, IL-6, IL-10, IL-11, IL-12, IL-13, L-22, IL-23, IL-27, IL-31, oncostatin M, ciliary neurotrophic factor, cardiotrophin 1, cardiotrophin-like cytokine, and LIF). The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. A genome-wide association study of 2,622 individuals with psoriasis identified associations between disease susceptibility and TYK2. Knockout or tyrphostin inhibition of TYK2 significantly reduces both IL-23 and IL-22-induced dermatitis.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6.

Decreased TYK2 activity leads to protection of joints from collagen antibody-induced arthritis, a model of human rheumatoid arthritis. Mechanistically, decreased Tyk2 activity reduced the production of Th1/Th17-related cytokines and matrix metalloproteases, and other key markers of inflammation.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. This corroborates earlier studies linking increased TYK2 expression with MS susceptibility. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Genome-wide association studies of individuals with SLE versus an unaffected cohort showed highly significant correlation between the TYK2 locus and SLE.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects.

Studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V7311), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform.

Thus, selective inhibition of TYK2 has been suggested as a suitable target for patients with IL-10 and/or BCL2-addicted tumors, such as 70% of adult T-cell leukemia cases. TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmortem brains of Alzheimer's patients.

Inhibition of JAK-STAT signaling pathways is also implicated in hair growth, and the reversal of the hair loss associated with alopecia areata.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Accordingly there is a need to provide novel inhibitors having more effective or advantageous pharmaceutically relevant properties, like selectivity over other JAK kinases (especially JAK2).

BRIEF SUMMARY OF THE INVENTION

Described herein are compounds that are useful in treating a TYK2-mediated disorder. In some embodiments, the TYK2-mediated disorder is an autoimmune disorder, an inflammatory disorder, a proliferative disorder, an endocrine disorder, a neurological disorder, or a disorder associated with transplantation. In some embodiments, the TYK2-mediated disorder is cancer.

Disclosed herein is a compound of Formula (I), or a pharmaceutically acceptable salt, solvate, or stereoisomer thereof:

Formula (I)

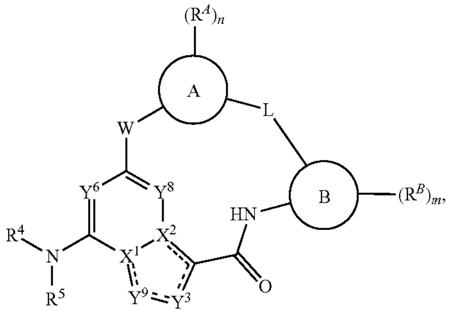

wherein:

L is a $C_1$-$C_4$alkylene; wherein one or two carbon atoms are optionally replaced by a heteroatom selected from oxygen, sulfur, nitrogen, or phosphate; and wherein L is optionally substituted with one or more $R^L$;

each $R^L$ is independently deuterium, halogen, —CN, —$OR^b$, —$NO_2$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl;

or two $R^L$ on the same carbon are taken together to form an oxo, a cycloalkyl, or a heterocycloalkyl;

Ring A is heteroaryl and Ring B is a cycloalkyl or a heterocycloalkyl;

or Ring A is aryl or heteroaryl and Ring B is a heterocycloalkyl or a 5- to 8-membered cycloalkyl;

each $R^A$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{A1}$;

each $R^{A1}$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl;

or two $R^{A1}$ on the same carbon are taken together to form an oxo;

n is 0-4;

each $R^B$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{B1}$;

or two $R^B$ on the same carbon are taken together to form an oxo;

each $R^{B1}$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl;

or two $R^{B1}$ on the same carbon are taken together to form an oxo;

m is 0-4;

$\overset{\cdot\cdot\cdot}{=}$ is a single bond or a double bond;

$X^1$ is N and $X^2$ is —C═ or $X^2$ is N and $X^1$ is —C═;

$Y^3$ is $CR^3$ or N;

$Y^6$ is $CR^6$ or N;

$Y^8$ is $CR^8$ or N;

$Y^9$ is $CR^9$ or N;

$R^3$, $R^6$, $R^8$, and $R^9$ are independently hydrogen, deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^4$ is hydrogen, $C_1$-$C_6$alkyl, $C_1$-$C_6$heteroalkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl are optionally substituted with one or more $R^{4a}$;

each $R^{4a}$ is independently deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl;

or two $R^{4a}$ on the same carbon are taken together to form an oxo;

$R^5$ is hydrogen, $C_1$-$C_6$alkyl, $C_1$-$C_6$haloalkyl, or $C_1$-$C_6$deuteroalkyl;

W is —O—, —S—, or —$NR^7$—;

$R^7$ is hydrogen, $C_1$-$C_6$alkyl, $C_1$-$C_6$haloalkyl, or $C_1$-$C_6$deuteroalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl; and each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl.

Also disclosed herein is a pharmaceutical composition comprising a therapeutically effective amount of the compound disclosed herein, or a pharmaceutically acceptable salt, stereoisomer, or solvate thereof, and a pharmaceutically acceptable excipient.

Also disclosed herein is a method of inhibiting a TYK2 enzyme in a patient or biological sample comprising contacting said patient or biological sample with a compound disclosed herein, or a pharmaceutically acceptable salt, stereoisomer, or solvate thereof.

Also disclosed herein is a method of treating a TYK2-mediated disorder comprising administering to a patient in need thereof a compound disclosed herein, or a pharmaceutically acceptable salt, stereoisomer, or solvate thereof. In some embodiments, the TYK2-mediated disorder is an autoimmune disorder, an inflammatory disorder, a proliferative disorder, an endocrine disorder, a neurological disorder, or a disorder associated with transplantation. In some embodiments, the disorder is associated with type I interferon, IL-10, IL-12, or IL-23 signaling.

INCORPORATION BY REFERENCE

All publications, patents, and patent applications mentioned in this specification are herein incorporated by reference for the specific purposes identified herein.

DETAILED DESCRIPTION OF THE INVENTION

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Oxo" refers to ═O.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to, ethenyl (—CH═$CH_2$), 1-propenyl (—$CH_2$CH═$CH_2$), isopropenyl [—C($CH_3$)═$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —Oalkyl wherein alkyl is as defined above. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Deuteroalkyl" refers to an alkyl radical, as defined above, that is substituted by one or more deuterium atoms. In some embodiments, the alkyl is substituted with one deuterium atom. In some embodiments, the alkyl is substituted with one, two, or three deuterium atoms. In some embodiments, the alkyl is substituted with one, two, three, four, five, or six deuterium atoms. Deuteroalkyl includes, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Haloalkyl" refers to an alkyl radical, as defined above, that is substituted by one or more halogen atoms. In some embodiments, the alkyl is substituted with one, two, or three halogen atoms. In some embodiments, the alkyl is substituted with one, two, three, four, five, or six halogen halogens. Haloalkyl includes, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

"Halo" or "halogen" refers to bromo, chloro, fluoro or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, $—CH_2OCH_3$, $—CH_2CH_2OCH_3$, $—CH_2CH_2OCH_2CH_2OCH_3$, or $—CH(CH_3)OCH_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, $—CF_3$, —OH, —OMe, $—NH_2$, or $—NO_2$. In some embodiments, a heteroalkyl is optionally substituted with oxo, halogen, methyl, ethyl, —CN, $—CF_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl comprises 1 or 2 heteroatoms selected from nitrogen and oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, $—CF_3$, —OH, —OMe, $—NH_2$, or $—NO_2$. In some embodiments, a heterocycloalkyl is optionally substituted with oxo, halogen, methyl, ethyl, —CN, $—CF_3$, —OH, or —OMe. In some embodiments, the heterocycloalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —$CF_3$, —OH, —OMe, —$NH_2$, or —$NO_2$. In some embodiments, a heteroaryl is optionally substituted with halogen, methyl, ethyl, —CN, —$CF_3$, —OH, or —OMe. In some embodiments, the heteroaryl is optionally substituted with halogen.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

As used herein, the term "TYK2-mediated" disorders, diseases, and/or conditions as used herein means any disease or other deleterious condition in which TYK2 or a mutant thereof is known to play a role. Accordingly, another embodiment relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

Compounds

Described herein are compounds that are useful in treating a TYK2-mediated disorder. In some embodiments, the TYK2-mediated disorder is an autoimmune disorder, an inflammatory disorder, a proliferative disorder, an endocrine disorder, a neurological disorder, or a disorder associated with transplantation. In some embodiments, the TYK2-mediated disorder is cancer.

Disclosed herein is a compound of Formula (I), or a pharmaceutically acceptable salt, solvate, or stereoisomer thereof:

Formula (I)

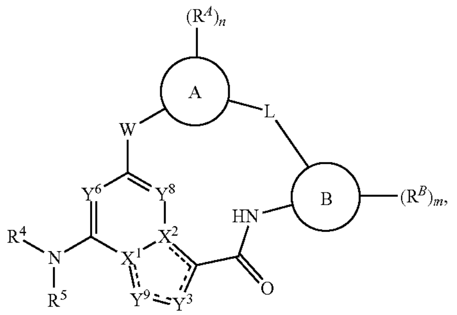

wherein:

L is a $C_1$-$C_4$alkylene; wherein one or two carbon atoms are optionally replaced by a heteroatom selected from oxygen, sulfur, nitrogen, or phosphate; and wherein L is optionally substituted with one or more $R^L$;

each $R^L$ is independently deuterium, halogen, —CN, —$OR^b$, —$NO_2$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl;

or two $R^L$ on the same carbon are taken together to form an oxo, a cycloalkyl, or a heterocycloalkyl;

Ring A is heteroaryl and Ring B is a cycloalkyl or a heterocycloalkyl;

or Ring A is aryl or heteroaryl and Ring B is a heterocycloalkyl or a 5- to 8-membered cycloalkyl;

each $R^A$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{A1}$;

each $R^{A1}$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═)

$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl;

or two $R^{A1}$ on the same carbon are taken together to form an oxo;

n is 0-4;

each $R^B$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{B1}$;

or two $R^B$ on the same carbon are taken together to form an oxo;

each $R^{B1}$ is independently deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl;

or two $R^{B1}$ on the same carbon are taken together to form an oxo;

m is 0-4;

═══ is a single bond or a double bond;

$X^1$ is N and $X^2$ is —C═ or $X^2$ is N and $X^1$ is —C═;

$Y^3$ is $CR^3$ or N;

$Y^6$ is $CR^6$ or N;

$Y^8$ is $CR^8$ or N;

$Y^9$ is $CR^9$ or N;

$R^3$, $R^6$, $R^8$, and $R^9$ are independently hydrogen, deuterium, halogen, —CN, —$OR^b$, —$SR^b$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^4$ is hydrogen, $C_1$-$C_6$alkyl, $C_1$-$C_6$heteroalkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl are optionally substituted with one or more $R^{4a}$;

each $R^{4a}$ is independently deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl;

or two $R^{4a}$ on the same carbon are taken together to form an oxo;

$R^5$ is hydrogen, $C_1$-$C_6$alkyl, $C_1$-$C_6$haloalkyl, or $C_1$-$C_6$deuteroalkyl;

W is —O—, —S—, or —$NR^7$—;

$R^7$ is hydrogen, $C_1$-$C_6$alkyl, $C_1$-$C_6$haloalkyl, or $C_1$-$C_6$deuteroalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl; and each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl.

In some embodiments, the compound of Formula (I) is of Formula (Ia), or a pharmaceutically acceptable salt, stereoisomer, or solvate thereof:

Formula (Ia)

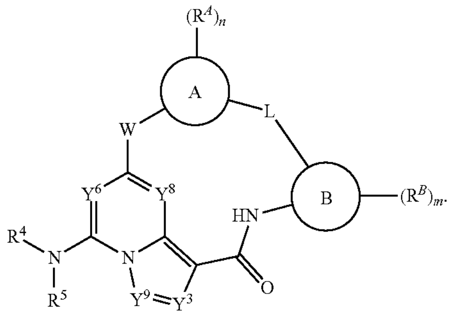

In some embodiments, the compound of Formula (I) is of Formula (Ib), or a pharmaceutically acceptable salt stereoisomer, or solvate thereof:

Formula (Ib)

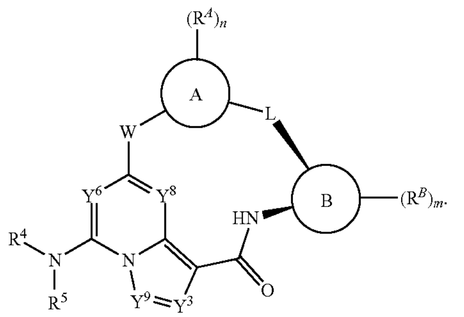

In some embodiments, the compound of Formula (I) is of Formula (Ic), or a pharmaceutically acceptable salt, stereoisomer, or solvate thereof:

Formula (Ic)

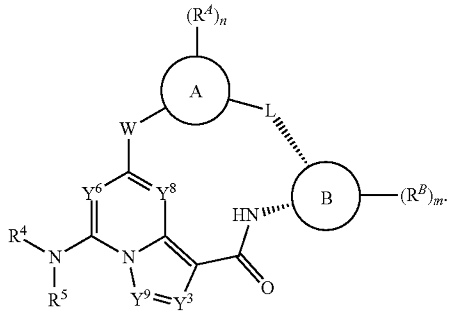

In some embodiments, the compound of Formula (I) is of Formula (Id), or a pharmaceutically acceptable salt, stereoisomer, or solvate thereof:

Formula (Id)

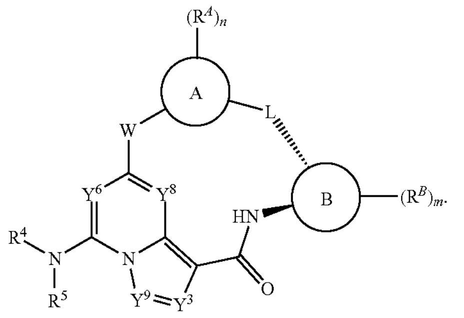

In some embodiments, the compound of Formula (I) is of Formula (Ie), or a pharmaceutically acceptable salt, stereoisomer, or solvate thereof:

Formula (Ie)

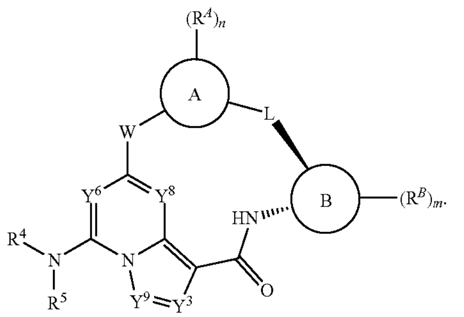

In some embodiments, the compound of Formula (I) is of Formula (If), or a pharmaceutically acceptable salt, stereoisomer, or solvate thereof:

Formula (If)

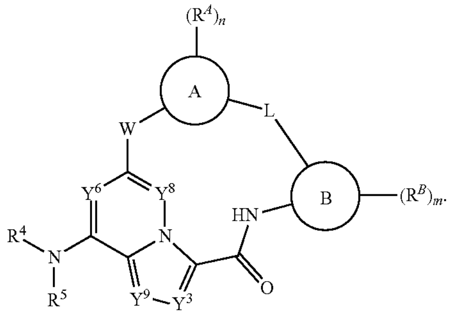

In some embodiments, the compound of Formula (I) is of Formula (Ig), or a pharmaceutically acceptable salt, stereoisomer, or solvate thereof:

Formula (Ig)

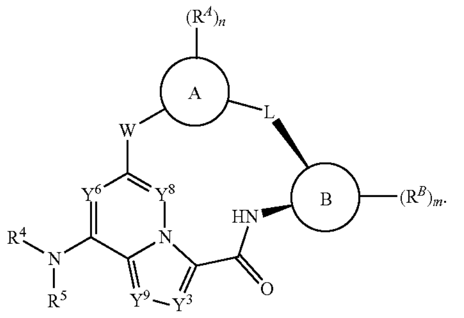

In some embodiments, the compound of Formula (I) is of Formula (Ih), or a pharmaceutically acceptable salt, stereoisomer, or solvate thereof:

Formula (Ih)

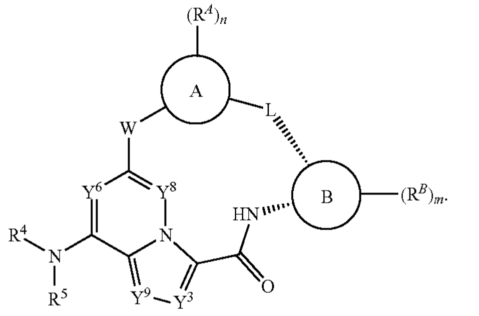

In some embodiments, the compound of Formula (I) is of Formula (Ii), or a pharmaceutically acceptable salt, stereoisomer, or solvate thereof:

Formula (Ii)

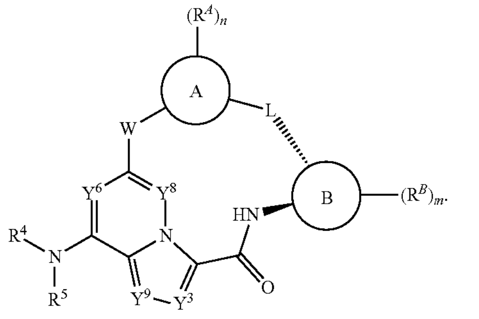

In some embodiments, the compound of Formula (I) is of Formula (Ij), or a pharmaceutically acceptable salt, stereoisomer, or solvate thereof:

Formula (Ij)

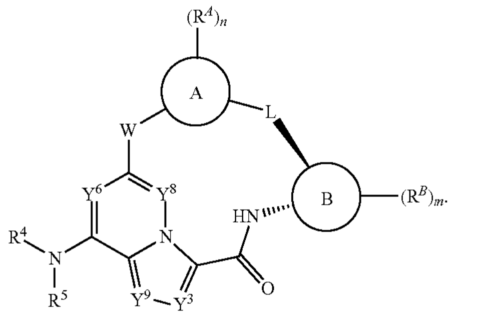

In some embodiments, the compound of Formula (I) is of Formula (Ik) or Formula (Il), or a pharmaceutically acceptable salt, stereoisomer, or solvate thereof:

(Ik)

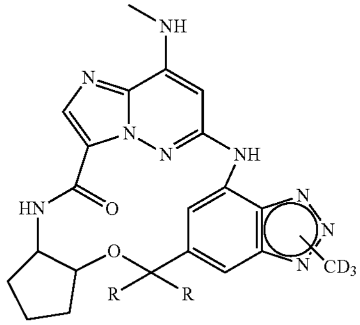

or (Il)

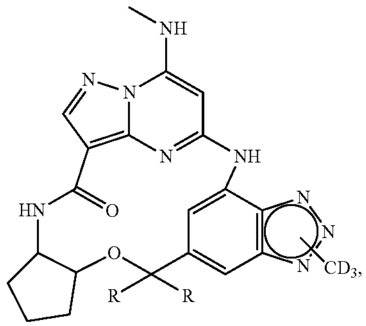

wherein at least each R is independently H or D, and at least one of R is D.

In some embodiments, the compound of Formula (I) is of Formula (Im) or Formula (In), or a pharmaceutically acceptable salt, stereoisomer, or solvate thereof:

(Im)

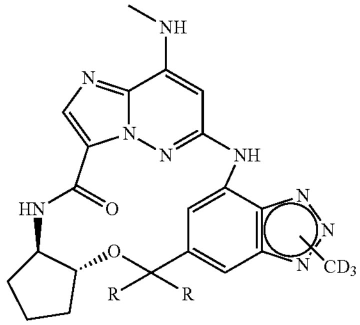

or (In)

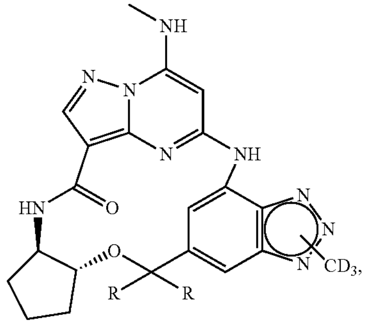

wherein at least each R is independently H or D, and at least one of R is D.

In some embodiments, the compound of Formula (I) is of Formula (Io) or Formula (Ip), or a pharmaceutically acceptable salt, stereoisomer, or solvate thereof:

(Io)

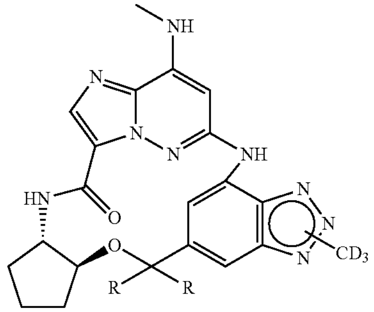

or (Ip)

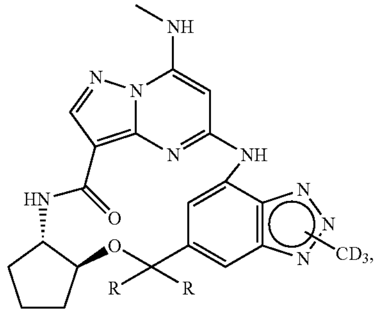

wherein at least each R is independently H or D, and at least one of R is D.

In some embodiments, the compound of Formula (I) is of Formula (Iq) or Formula (Ir), or a pharmaceutically acceptable salt, stereoisomer, or solvate thereof:

(Iq)

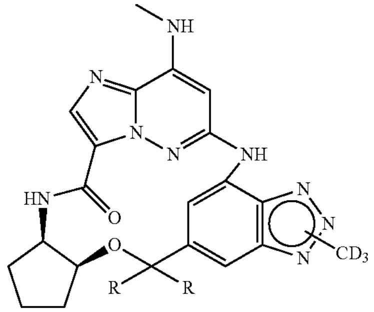

or (Ir)

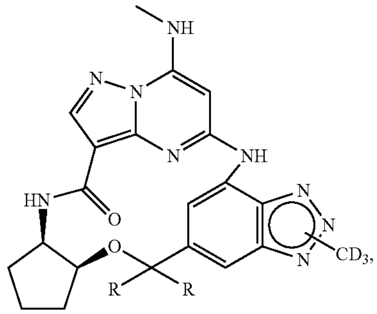

wherein at least each R is independently H or D, and at least one of R is D.

In some embodiments, the compound of Formula (I) is of Formula (Is) or Formula (It), or a pharmaceutically acceptable salt, stereoisomer, or solvate thereof:

(Is)

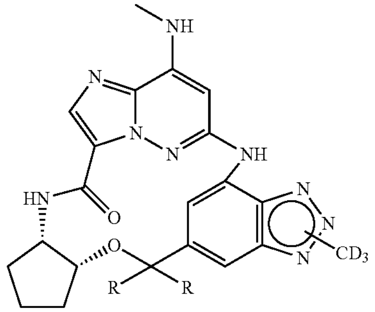

or (It)

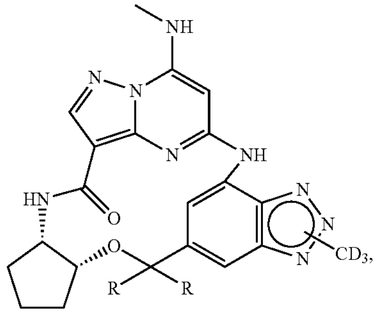

wherein at least each R is independently H or D, and at least one of R is D.

In some embodiments of a compound of Formula (I) or (Ia)-(Ij), or a pharmaceutically acceptable salt, stereoisomer, or solvate thereof, Ring A is heteroaryl and Ring B is a cycloalkyl or a heterocycloalkyl.

In some embodiments of a compound of Formula (I) or (Ia)-(Ij), or a pharmaceutically acceptable salt, stereoisomer, or solvate thereof, Ring A is aryl or heteroaryl and Ring B is a heterocycloalkyl.

In some embodiments of a compound of Formula (I) or (Ia)-(Ij), or a pharmaceutically acceptable salt, stereoisomer, or solvate thereof, Ring A is aryl or heteroaryl and Ring B is a 5- to 8-membered cycloalkyl.

In some embodiments of a compound of Formula (I) or (Ia)-(Ij), or a pharmaceutically acceptable salt, stereoisomer, or solvate thereof, Ring B is a 5- to 6-membered cycloalkyl.

In some embodiments of a compound of Formula (I) or (Ia)-(Ij), or a pharmaceutically acceptable salt, stereoisomer, or solvate thereof, Ring B is a 5-membered cycloalkyl.

In some embodiments of a compound of Formula (I) or (Ia)-(Ij), or a pharmaceutically acceptable salt, stereoisomer, or solvate thereof, Ring B is a 5- to 6-membered heterocycloalkyl.

In some embodiments of a compound of Formula (I) or (Ia)-(Ij), or a pharmaceutically acceptable salt, stereoisomer, or solvate thereof, Ring B is a 5-membered heterocycloalkyl. In some embodiments of a compound of Formula (I) or (Ia)-(Ij), or a pharmaceutically acceptable salt, stereoisomer, or solvate thereof, Ring B is a tetrahydrofuran or pyrrolidine. In some embodiments of a compound of Formula (I) or (Ia)-(Ij), or a pharmaceutically acceptable salt, stereoisomer, or solvate thereof, Ring B is a tetrahydrofuran.

In some embodiments of a compound of Formula (I) or (Ia)-(Ij), or a pharmaceutically acceptable salt, stereoisomer, or solvate thereof, Ring A is a bicyclic heteroaryl. In some embodiments of a compound of Formula (I) or (Ia)-(Ij), or a pharmaceutically acceptable salt, stereoisomer, or solvate thereof, Ring A is indolyl, indazolyl, benzimidazolyl, benzotriazolyl, benzothiophenyl, benzothiazolyl, benzofuranyl, or benzoxazolyl.

In some embodiments of a compound of Formula (I) or (Ia)-(Ij), or a pharmaceutically acceptable salt, stereoisomer, or solvate thereof, Ring A is a monocyclic heteroaryl. In some embodiments of a compound of Formula (I) or (Ia)-(Ij), or a pharmaceutically acceptable salt, stereoisomer, or solvate thereof, Ring A is pyridyl, pyrimidyl, pyrazinyl, or pyridazinyl.

In some embodiments of a compound of Formula (I) or (Ia)-(Ij), or a pharmaceutically acceptable salt, stereoisomer, or solvate thereof, Ring A is phenyl.

In some embodiments of a compound of Formula (I) or (Ia)-(Ij), or a pharmaceutically acceptable salt, stereoisomer, or solvate thereof, $Y^9$ is N. In some embodiments of a compound of Formula (I) or (Ia)-(Ij), or a pharmaceutically acceptable salt, stereoisomer, or solvate thereof, $Y^9$ is $CR^9$. In some embodiments of a compound of Formula (I) or (Ia)-(Ij), or a pharmaceutically acceptable salt, stereoisomer, or solvate thereof, $R^9$ is hydrogen, deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (I) or (Ia)-(Ij), or a pharmaceutically acceptable salt, stereoisomer, or solvate thereof, $R^9$ is hydrogen, deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, $R^9$ is hydrogen, deuterium, halogen, or $C_1$-$C_6$alkyl. In some embodiments of a compound of Formula (I) or (Ia)-(Ij), or a pharmaceutically acceptable salt, stereoisomer, or solvate thereof, $R^9$ is hydrogen, halogen, or $C_1$-$C_6$alkyl. In some embodiments of a compound of Formula (I) or (Ia)-(Ij), or a pharmaceutically acceptable salt, stereoisomer, or solvate thereof, $R^9$ is hydrogen.

In some embodiments of a compound of Formula (I) or (Ia)-(Ij), or a pharmaceutically acceptable salt, stereoisomer, or solvate thereof, $Y^6$ is N. In some embodiments of a compound of Formula (I) or (Ia)-(Ij), or a pharmaceutically acceptable salt, stereoisomer, or solvate thereof, $Y^6$ is $CR^6$. In some embodiments of a compound of Formula (I) or (Ia)-(Ij), or a pharmaceutically acceptable salt, stereoisomer, or solvate thereof, $R^6$ is hydrogen, deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (I) or (Ia)-(Ij), or a pharmaceutically acceptable salt, stereoisomer, or solvate thereof, $R^6$ is hydrogen, deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, $R^6$ is hydrogen, deuterium, halogen, or $C_1$-$C_6$alkyl. In some embodiments of a compound of Formula (I) or (Ia)-(Ij), or a pharmaceutically acceptable salt, stereoisomer, or solvate thereof, $R^6$ is hydrogen, halogen, or $C_1$-$C_6$alkyl. In some embodiments of a compound of Formula (I) or (Ia)-(Ij), or a pharmaceutically acceptable salt, stereoisomer, or solvate thereof, $R^6$ is hydrogen.

In some embodiments of a compound of Formula (I) or (Ia)-(Ij), or a pharmaceutically acceptable salt, stereoisomer, or solvate thereof, $Y^3$ is N. In some embodiments of a compound of Formula (I) or (Ia)-(Ij), or a pharmaceutically acceptable salt, stereoisomer, or solvate thereof, $Y^3$ is $CR^3$. In some embodiments of a compound of Formula (I) or (Ia)-(Ij), or a pharmaceutically acceptable salt, stereoisomer, or solvate thereof, $R^3$ is hydrogen, deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (I) or (Ia)-(Ij), or a pharmaceutically acceptable salt, stereoisomer, or solvate thereof, $R^3$ is hydrogen, deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, $R^3$ is hydrogen, deuterium, halogen, or $C_1$-$C_6$alkyl. In some embodiments of a compound of Formula (I) or (Ia)-(Ij), or a pharmaceutically acceptable salt, stereoisomer, or solvate thereof, $R^3$ is hydrogen, halogen, or $C_1$-$C_6$alkyl. In some embodiments of a compound of Formula (I) or (Ia)-(Ij), or a pharmaceutically acceptable salt, stereoisomer, or solvate thereof, $R^3$ is hydrogen.

In some embodiments of a compound of Formula (I) or (Ia)-(Ij), or a pharmaceutically acceptable salt, stereoisomer, or solvate thereof, $Y^8$ is N. In some embodiments of a compound of Formula (I) or (Ia)-(Ij), or a pharmaceutically acceptable salt, stereoisomer, or solvate thereof, $Y^8$ is CR. In some embodiments of a compound of Formula (I) or (Ia)-(Ij), or a pharmaceutically acceptable salt, stereoisomer, or solvate thereof, $R^8$ is hydrogen, deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (I) or (Ia)-(Ij), or a pharmaceutically acceptable salt, stereoisomer, or solvate thereof, $R^8$ is hydrogen, deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, $R^8$ is hydrogen, deuterium, halogen, or $C_1$-$C_6$alkyl. In some embodiments of a compound of Formula (I) or (Ia)-(Ij), or a pharmaceutically acceptable salt, stereoisomer, or solvate thereof, $R^8$ is hydrogen, halogen, or $C_1$-$C_6$alkyl. In some embodiments of a compound of Formula (I) or (Ia)-(Ij), or a pharmaceutically acceptable salt, stereoisomer, or solvate thereof, $R^8$ is hydrogen.

In some embodiments of a compound of Formula (I) or (Ia)-(Ij), or a pharmaceutically acceptable salt, stereoisomer, or solvate thereof, $R^4$ is hydrogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, $R^4$ is $C_1$-$C_6$alkyl or $C_1$-$C_6$deuteroalkyl.

In some embodiments of a compound of Formula (I) or (Ia)-(Ij), or a pharmaceutically acceptable salt, stereoisomer, or solvate thereof, $R^5$ is hydrogen, $C_1$-$C_6$alkyl, $C_1$-$C_6$haloalkyl, or $C_1$-$C_6$deuteroalkyl.

In some embodiments of a compound of Formula (I) or (Ia)-(Ij), or a pharmaceutically acceptable salt, stereoisomer, or solvate thereof, $R^5$ is $C_1$-$C_6$alkyl or $C_1$-$C_6$deuteroalkyl. In some embodiments of a compound of Formula (I) or (Ia)-(Ij), or a pharmaceutically acceptable salt, stereoisomer, or solvate thereof, R is hydrogen.

In some embodiments of a compound of Formula (I) or (Ia)-(Ij), or a pharmaceutically acceptable salt, stereoisomer, or solvate thereof, W is —S—. In some embodiments of a compound of Formula (I) or (Ia)-(Ij), or a pharmaceutically acceptable salt, stereoisomer, or solvate thereof, W is —O—.

In some embodiments of a compound of Formula (I) or (Ia)-(Ij), or a pharmaceutically acceptable salt, stereoisomer, or solvate thereof, W is —$NR^7$—. In some embodiments of a compound of Formula (I) or (Ia)-(Ij), or a pharmaceutically acceptable salt, stereoisomer, or solvate thereof, $R^7$ is hydrogen or $C_1$-$C_6$alkyl. In some embodiments of a compound of Formula (I) or (Ia)-(Ij), or a pharmaceutically acceptable salt, stereoisomer, or solvate thereof, $R^7$ is hydrogen. In some embodiments of a compound of Formula (I) or (Ia)-(Ij), or a pharmaceutically acceptable salt, stereoisomer, or solvate thereof, $R^7$ is $C_1$-$C_6$alkyl.

In some embodiments of a compound of Formula (I) or (Ia)-(Ij), or a pharmaceutically acceptable salt, stereoisomer, or solvate thereof, each $R^A$ is independently deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more $R^{A1}$. In some embodiments of a compound of Formula (I) or (Ia)-(Ij), or a pharmaceutically acceptable salt, stereoisomer, or solvate thereof, each $R^A$ is independently deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more $R^{A1}$. In some embodiments of a compound of Formula (I) or (Ia)-(Ij), or a pharmaceutically acceptable salt, stereoisomer, or solvate thereof, each $R^A$ is independently deuterium, halogen, $C_1$-$C_6$alkyl, $C_1$-$C_6$haloalkyl, $C_1$-$C_6$deuteroalkyl, aryl, or heteroaryl; wherein each alkyl, aryl, and heteroaryl is independently optionally substituted with one or more $R^{A1}$. In some embodiments of a compound of Formula (I) or (Ia)-(Ij), or a pharmaceutically acceptable salt, stereoisomer, or solvate thereof, each $R^A$ is independently deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^A$ is independently $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^A$ is independently $C_1$-$C_6$deuteroalkyl.

In some embodiments of a compound of Formula (I) or (Ia)-(Ij), or a pharmaceutically acceptable salt, stereoisomer, or solvate thereof, each $R^{A1}$ is independently deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I) or (Ia)-(Ij), or a pharmaceutically acceptable salt, stereoisomer, or solvate thereof, each $R^{A1}$ is independently deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^{A1}$ is independently deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^{A1}$ is independently deuterium, halogen, or $C_1$-$C_6$alkyl.

In some embodiments of a compound of Formula (I) or (Ia)-(Ij), or a pharmaceutically acceptable salt, stereoisomer, or solvate thereof, n is 0-2. In some embodiments of a compound of Formula (I) or (Ia)-(Ij), or a pharmaceutically acceptable salt, stereoisomer, or solvate thereof, n is 0 or 1. In some embodiments of a compound of Formula (I) or (Ia)-(Ij), or a pharmaceutically acceptable salt, stereoisomer, or solvate thereof, n is 1 or 2. In some embodiments of a compound of Formula (I) or (Ia)-(Ij), or a pharmaceutically acceptable salt, stereoisomer, or solvate thereof, n is 0. In some embodiments of a compound of Formula (I) or (Ia)-(Ij), or a pharmaceutically acceptable salt, stereoisomer, or solvate thereof, n is 1. In some embodiments of a compound of Formula (I) or (Ia)-(Ij), or a pharmaceutically acceptable salt, stereoisomer, or solvate thereof, n is 2. In some embodiments of a compound of Formula (I) or (Ia)-(Ij), or a pharmaceutically acceptable salt, stereoisomer, or solvate thereof, n is 3.

In some embodiments of a compound of Formula (I) or (Ia)-(Ij), or a pharmaceutically acceptable salt, stereoisomer, or solvate thereof, each $R^B$ is independently deuterium, halogen, —CN, —$OR^b$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more $R^{B1}$. In some embodiments of a compound of Formula (I) or (Ia)-(Ij), or a pharmaceutically acceptable salt, stereoisomer, or solvate thereof, each $R^B$ is independently deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more $R^B$. In some embodiments of a compound of Formula (I) or (Ia)-(Ij), or a pharmaceutically acceptable salt, stereoisomer, or solvate thereof, each $R^B$ is independently deuterium, halogen, $C_1$-$C_6$alkyl, $C_1$-$C_6$haloalkyl, $C_1$-$C_6$deuteroalkyl, aryl, or heteroaryl; wherein each alkyl, aryl, and heteroaryl is independently optionally substituted with one or more $R^{B1}$. In some embodiments of a compound of Formula (I) or (Ia)-(Ij), or a pharmaceutically acceptable salt, stereoisomer, or solvate thereof, each $R^B$ is independently deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^B$ is independently $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^B$ is independently $C_1$-$C_6$alkyl.

In some embodiments of a compound of Formula (I) or (Ia)-(Ij), or a pharmaceutically acceptable salt, stereoisomer, or solvate thereof, each $R^{B1}$ is independently deuterium, halogen, —CN, —$OR^b$, —$NR^cR^d$, —C(═O)$R^a$, —C(═)$OR^b$, —C(═O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I) or (Ia)-(Ij), or a pharmaceutically acceptable salt, stereoisomer, or solvate thereof, each $R^{B1}$ is independently deuterium, halogen, —CN, —$OR^b$, —$NR^cR^d$, —C(═O)$R^a$, —C(═O)$OR^b$, —C(═O)NR$^c$R$^d$, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^{B1}$ is independently deuterium, halogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^{B1}$ is independently deuterium, halogen, or $C_1$-$C_6$alkyl.

In some embodiments of a compound of Formula (I) or (Ia)-(Ij), or a pharmaceutically acceptable salt, stereoisomer, or solvate thereof, m is 0-2. In some embodiments of a compound of Formula (I) or (Ia)-(Ij), or a pharmaceutically acceptable salt, stereoisomer, or solvate thereof, m is 0 or 1. In some embodiments of a compound of Formula (I) or (Ia)-(Ij), or a pharmaceutically acceptable salt, stereoisomer, or solvate thereof, m is 1 or 2. In some embodiments of a compound of Formula (I) or (Ia)-(Ij), or a pharmaceutically acceptable salt, stereoisomer, or solvate thereof, m is 0. In some embodiments of a compound of Formula (I) or (Ia)-(Ij), or a pharmaceutically acceptable salt, stereoisomer, or solvate thereof, m is 1. In some embodiments of a compound of Formula (I) or (Ia)-(Ij), or a pharmaceutically acceptable salt, stereoisomer, or solvate thereof, m is 2. In some embodiments of a compound of Formula (I) or (Ia)-(Ij), or a pharmaceutically acceptable salt, stereoisomer, or solvate thereof, m is 3.

In some embodiments of a compound of Formula (I) or (Ia)-(Ij), or a pharmaceutically acceptable salt, stereoisomer, or solvate thereof, L is a $C_2$-$C_4$alkylene; wherein one carbon atom is optionally replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_4$alkylene; wherein one carbon atom is optionally replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_4$alkylene; wherein one carbon atom is optionally replaced by an oxygen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_4$alkylene; wherein one carbon atom is replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_4$alkylene; wherein one carbon atom is replaced by a heteroatom selected from oxygen or sulfur; and wherein L is optionally substituted with one or more $R^L$.

In some embodiments of a compound of Formula (I) or (Ia)-(Ij), or a pharmaceutically acceptable salt, stereoisomer, or solvate thereof, L is a $C_2$-$C_4$alkylene; wherein one carbon atom is replaced by an oxygen; and wherein L is optionally substituted with one or more $R^L$.

In some embodiments of a compound of Formula (I) or (Ia)-(Ij), or a pharmaceutically acceptable salt, stereoisomer, or solvate thereof, L is a $C_2$-$C_3$alkylene; wherein one carbon atom is optionally replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_3$alkylene; wherein one carbon atom is optionally replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_3$alkylene; wherein one carbon atom is optionally replaced by an oxygen atom; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_3$alkylene; wherein one carbon atom is replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_3$alkylene; wherein one carbon atom is replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-$C_3$alkylene; wherein one carbon atom is optionally replaced by an oxygen atom; and wherein L is optionally substituted with one or more $R^L$.

In some embodiments of a compound of Formula (I) or (Ia)-(Ij), or a pharmaceutically acceptable salt, stereoisomer, or solvate thereof, L is a $C_3$-alkylene; wherein one carbon atom is optionally replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_3$-alkylene; wherein one carbon atom is optionally replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_3$-alkylene; wherein one carbon atom is optionally replaced by an oxygen atom; and wherein L is optionally substituted with one or more $R^L$. In some embodiments of a compound of Formula (I) or (Ia)-(Ij), or a pharmaceutically acceptable salt, stereoisomer, or solvate thereof, L is a $C_3$-alkylene; wherein one carbon atom is replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_3$-alkylene; wherein one carbon atom is replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_3$-alkylene; wherein one carbon atom is replaced by an oxygen atom; and wherein L is optionally substituted with one or more $R^L$.

In some embodiments of a compound of Formula (I) or (Ia)-(Ij), or a pharmaceutically acceptable salt, stereoisomer, or solvate thereof, L is a $C_2$-alkylene; wherein one carbon atom is optionally replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-alkylene; wherein one carbon atom is optionally replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-alkylene; wherein one carbon atom is optionally replaced by an oxygen atom; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-alkylene; wherein one carbon atom is replaced by a heteroatom selected from oxygen, sulfur, or nitrogen; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-alkylene; wherein one carbon atom is replaced by a heteroatom selected from oxygen or sulfur; and wherein L is optionally substituted with one or more $R^L$. In some embodiments of a compound of Formula (I) or (Ia)-(Ij), or a pharmaceutically acceptable salt, stereoisomer, or solvate thereof, L is a $C_2$-alkylene; wherein one carbon atom is replaced by an oxygen atom; and wherein L is optionally substituted with one or more $R^L$.

In some embodiments of a compound of Formula (I) or (Ia)-(Ij), or a pharmaceutically acceptable salt, stereoisomer, or solvate thereof, each $R^L$ is independently deuterium, halogen, —CN, —$OR^b$, —$NR^cR^d$, —C(═O)$R^a$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl; or two $R^L$ on the same carbon are taken together to form an oxo, a cycloalkyl, or a heterocycloalkyl. In some embodiments of a compound of Formula (I) or (Ia)-(Ij), or a pharmaceutically acceptable salt, stereoisomer, or solvate thereof, each $R^L$ is independently deuterium, halogen, $C_1$-$C_6$alkyl, $C_1$-$C_6$haloalkyl, or $C_1$-$C_6$deuteroalkyl; or two $R^L$ on the same carbon are taken together to form an oxo, a cycloalkyl, or a heterocycloalkyl. In some embodiments of a compound of Formula (I) or (Ia)-(Ij), or a pharmaceutically acceptable salt, stereoisomer, or solvate thereof, each $R^L$ is independently deuterium, halogen, $C_1$-$C_6$alkyl, $C_1$-$C_6$haloalkyl, or $C_1$-$C_6$deuteroalkyl.

In some embodiments of a compound of Formula (I) or (Ia)-(Ij), or a pharmaceutically acceptable salt, stereoisomer, or solvate thereof, L is —$CH_2$—O—, —O—$CH_2$—, —$CH_2$—S—, or —S—$CH_2$—. In some embodiments of a compound of Formula (I) or (Ia)-(Ij), or a pharmaceutically acceptable salt, stereoisomer, or solvate thereof, L is —$CH_2$—O— or —O—$CH_2$—.

In some embodiments of a compound of Formula (I) or (Ia)-(Ij), or a pharmaceutically acceptable salt, stereoisomer, or solvate thereof, each $R^a$ is independently $C_1$-$C_6$alkyl, $C_1$-$C_6$haloalkyl, $C_1$-$C_6$deuteroalkyl, or cycloalkyl; wherein each alkyl and cycloalkyl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl. In some embodiments of a compound of Formula (I) or (Ia)-(Ij), or a pharmaceutically acceptable salt, stereoisomer, or solvate thereof, each $R^a$ is independently $C_1$-$C_6$alkyl, $C_1$-$C_6$haloalkyl, or $C_1$-$C_6$deuteroalkyl. In some embodiments of a compound described above, each $R^a$ is independently $C_1$-$C_6$alkyl.

In some embodiments of a compound of Formula (I) or (Ia)-(Ij), or a pharmaceutically acceptable salt, stereoisomer, or solvate thereof, each $R^b$ is independently hydrogen, $C_1$-$C_6$alkyl, $C_1$-$C_6$haloalkyl, $C_1$-$C_6$deuteroalkyl, or cycloalkyl; wherein each alkyl and cycloalkyl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl. In some embodiments of a compound of Formula (I) or (Ia)-(Ij), or a pharmaceutically acceptable salt, stereoisomer, or solvate thereof, each $R^b$ is independently hydrogen, $C_1$-$C_6$alkyl, $C_1$-$C_6$haloalkyl, or $C_1$-$C_6$deuteroalkyl. In some embodiments of a compound described above, each $R^b$ is independently hydrogen or $C_1$-$C_6$alkyl. In some embodiments of a compound described above, each $R^b$ is hydrogen. In some embodiments of a compound of Formula (I) or (Ia)-(Ij), or a pharmaceutically acceptable salt, stereoisomer, or solvate thereof, each $R^b$ is independently $C_1$-$C_6$alkyl.

In some embodiments of a compound of Formula (I) or (Ia)-(Ij), or a pharmaceutically acceptable salt, stereoisomer, or solvate thereof, each $R^c$ and $R^d$ is independently hydrogen, $C_1$-$C_6$alkyl, $C_1$-$C_6$haloalkyl, $C_1$-$C_6$deuteroalkyl, or cycloalkyl; wherein each alkyl and cycloalkyl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl. In some embodiments of a compound of Formula (I) or (Ia)-(Ij), or a pharmaceutically acceptable salt, stereoisomer, or solvate thereof, each $R^c$ and $R^d$ is independently hydrogen, $C_1$-$C_6$alkyl, $C_1$-$C_6$haloalkyl, or $C_1$-$C_6$deuteroalkyl. In some embodiments of a compound of Formula (I) or (Ia)-(Ij), or a pharmaceutically acceptable salt, stereoisomer, or solvate thereof, each $R^c$ and $R^d$ is independently hydrogen or $C_1$-$C_6$alkyl. In some embodiments of a compound described above, each $R^c$ and $R^d$ is hydrogen. In some embodiments of a compound of Formula (I) or (Ia)-(Ij), or a pharmaceutically acceptable salt, stereoisomer, or solvate thereof, each $R^c$ and $R^d$ is independently $C_1$-$C_6$alkyl.

In some embodiments of a compound of Formula (I) or (Ia)-(Ij), or a pharmaceutically acceptable salt, stereoisomer, or solvate thereof, each L, $R^A$, $R^B$, $R^4$, $R^a$, $R^b$, $R^c$, and $R^d$ is independently substituted with one, two, three, or four substituents as defined herein. In some embodiments of a compound of Formula (I) or (Ia)-(Ij), or a pharmaceutically acceptable salt, stereoisomer, or solvate thereof, each L, $R^A$, $R^B$, $R^4$, $R^a$, $R^b$, $R^c$, and $R^d$ is independently optionally substituted with one, two, or three substituents as defined herein. In some embodiments of a compound of Formula (I) or (Ia)-(Ij), or a pharmaceutically acceptable salt, stereoisomer, or solvate thereof, each L, $R^A$, $R^B$, $R^4$, $R^a$, $R^b$, $R^c$, and $R^d$ is independently optionally substituted with one or two substituents as defined herein. In some embodiments of a compound of Formula (I) or (Ia)-(Ij), or a pharmaceutically acceptable salt, stereoisomer, or solvate thereof, each L, $R^A$, $R^B$, $R^4$, $R^a$, $R^b$, $R^c$, and $R^d$ is independently optionally substituted with one substituent as defined herein.

In some embodiments of a compound of Formula (I) or (Ia)-(Ij), or a pharmaceutically acceptable salt, stereoisomer, or solvate thereof, the compound is selected from:

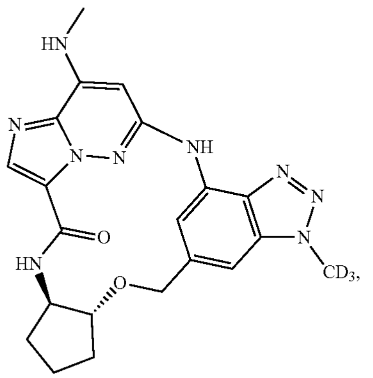

-continued
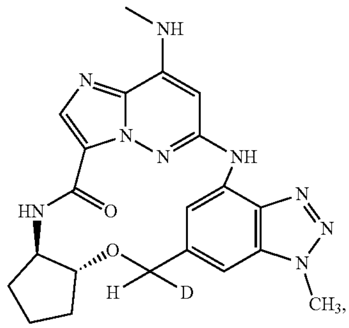
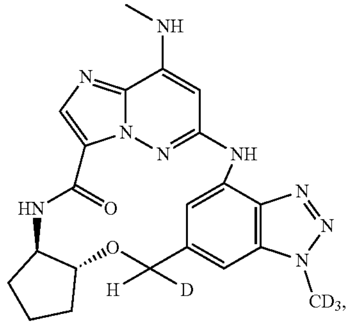
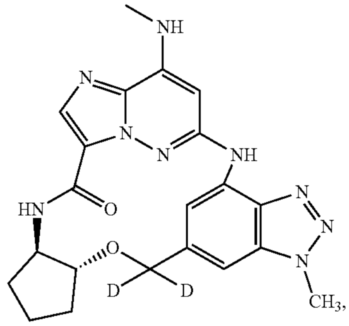
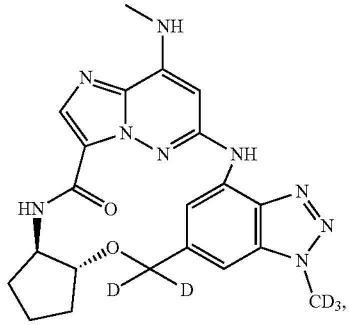
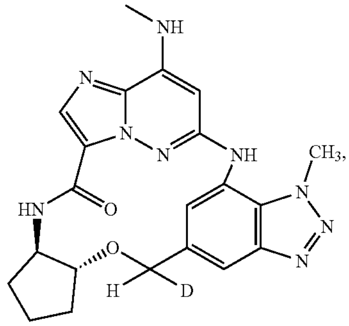
-continued
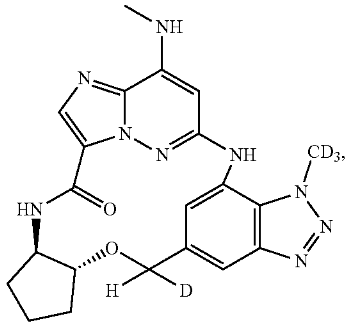
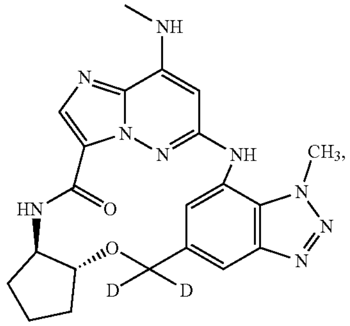
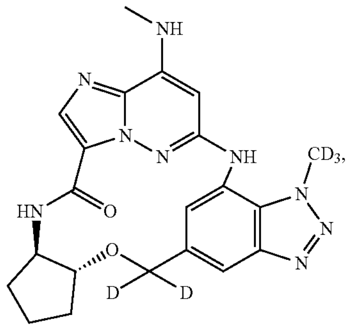
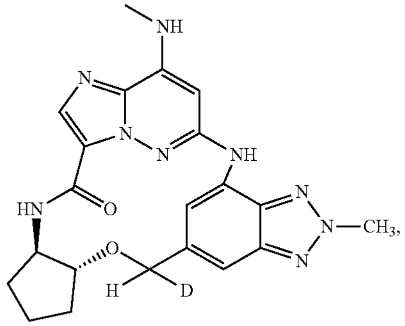
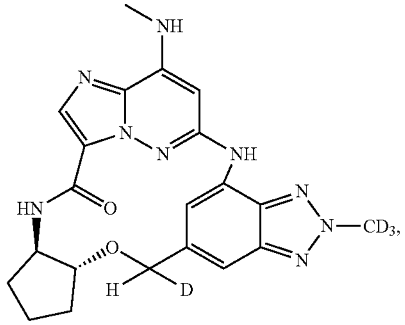

-continued
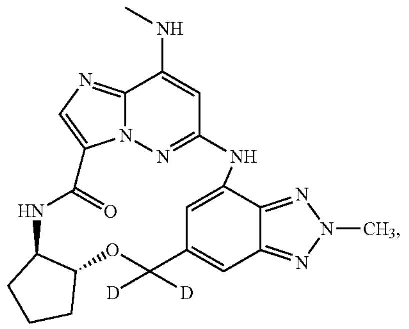
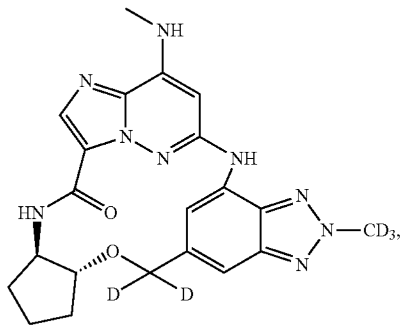
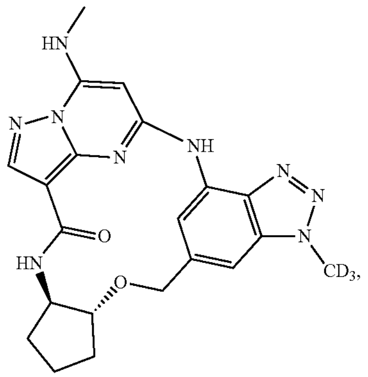
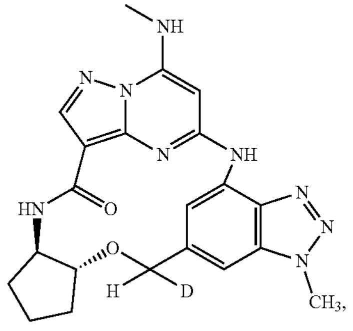
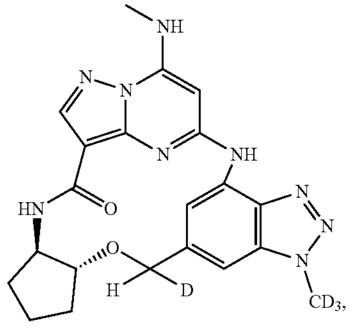
-continued
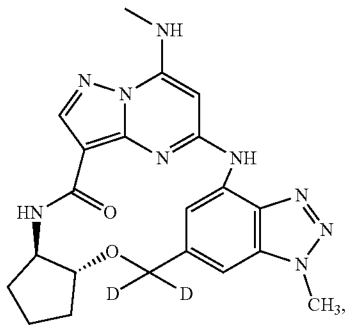
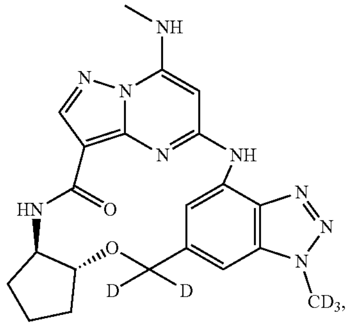
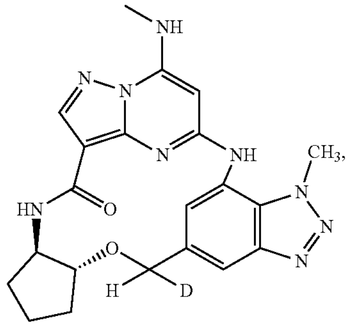
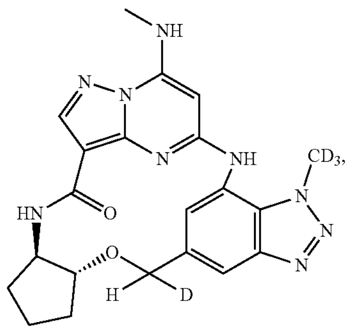
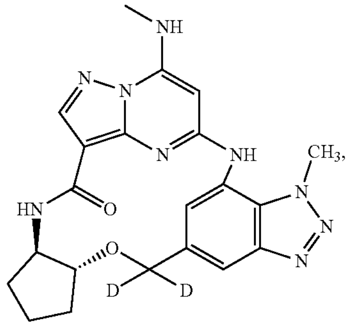

-continued
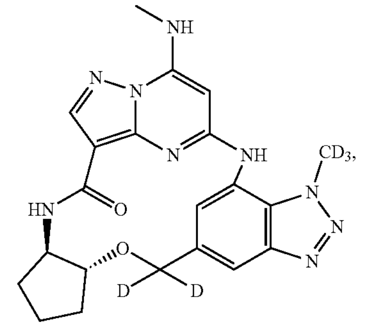
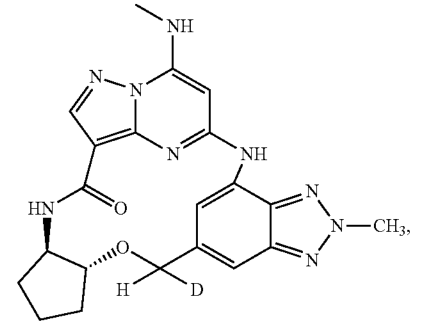
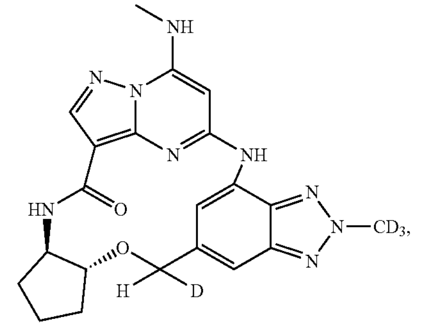
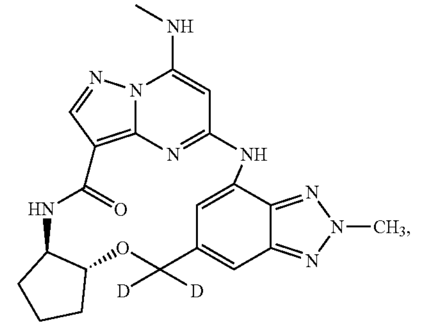
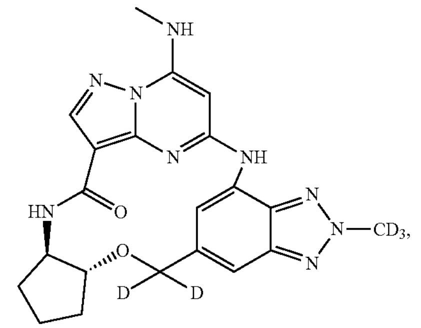
-continued
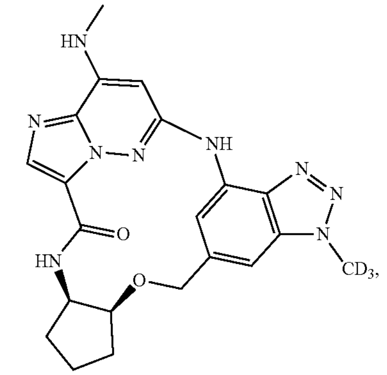
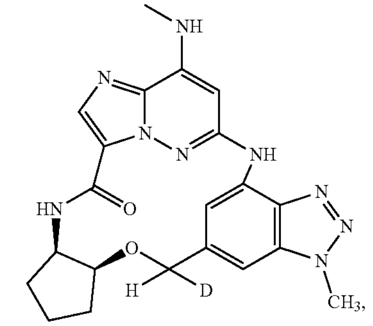
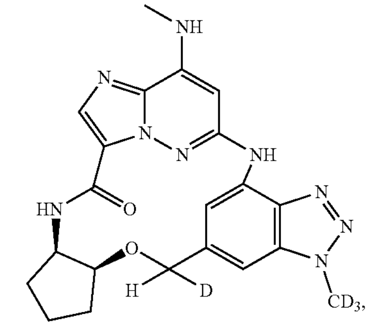
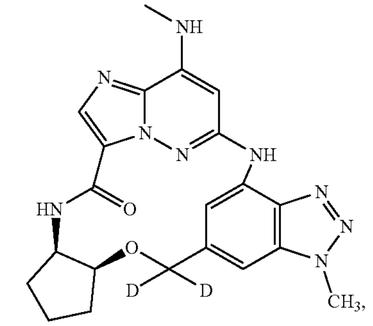
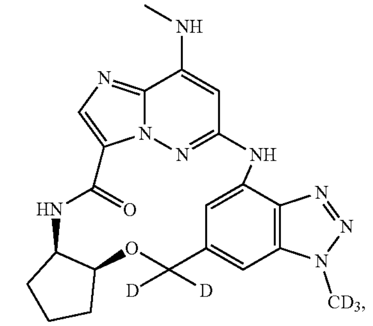

-continued
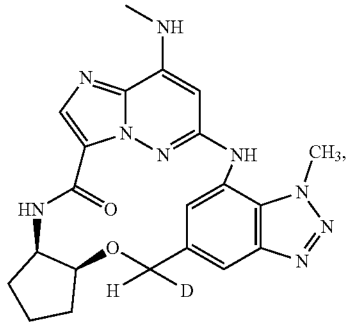
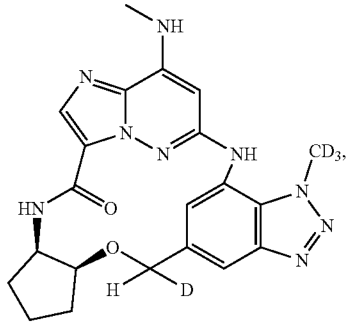
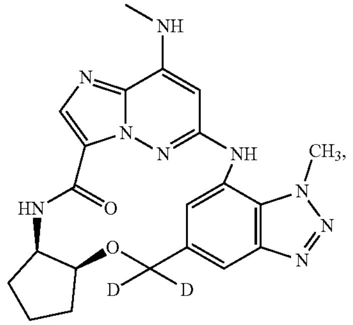
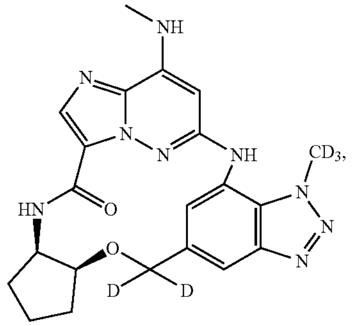
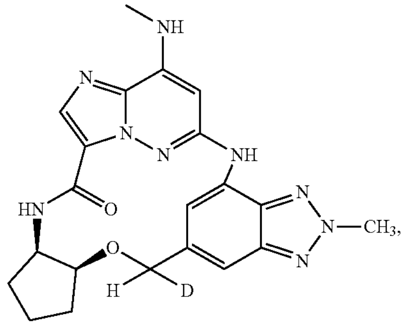
-continued
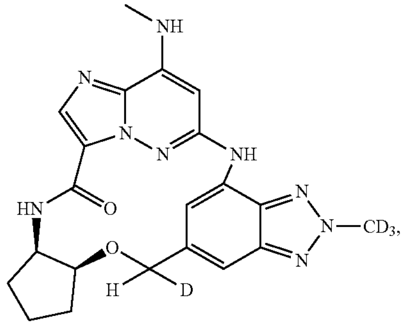
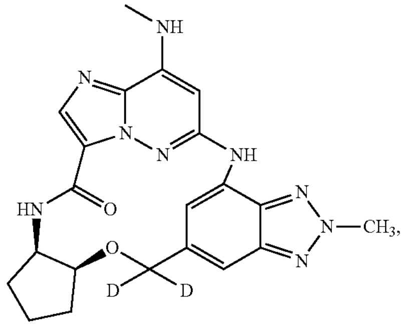
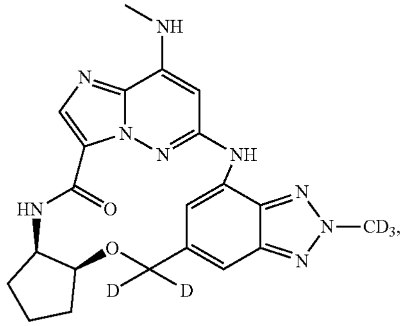
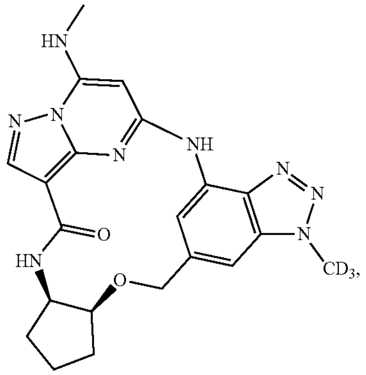
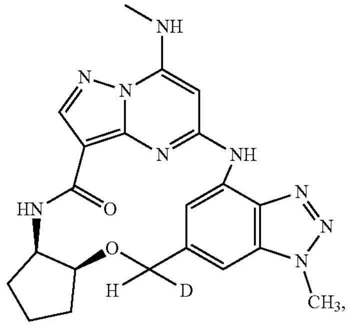

-continued
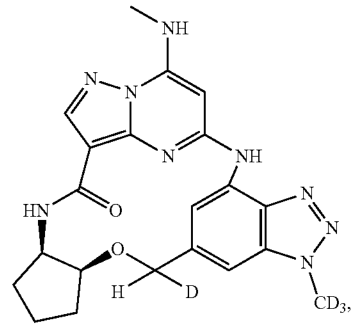
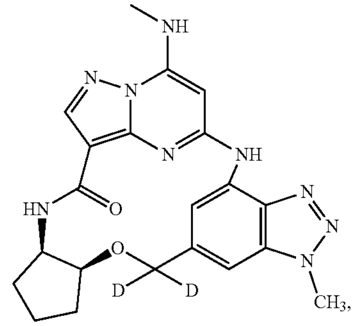
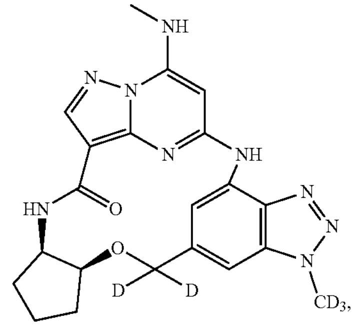
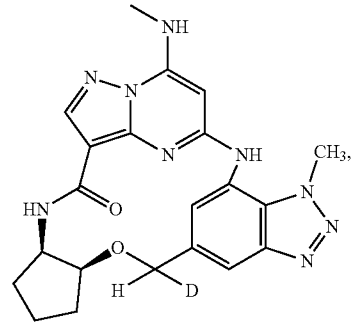
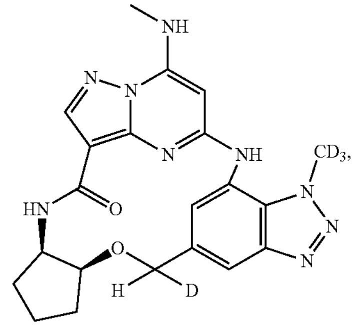
-continued
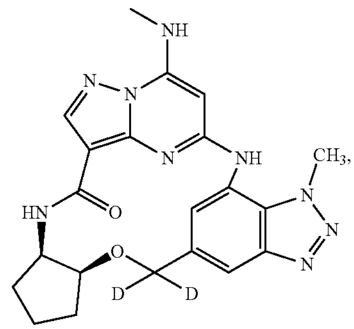
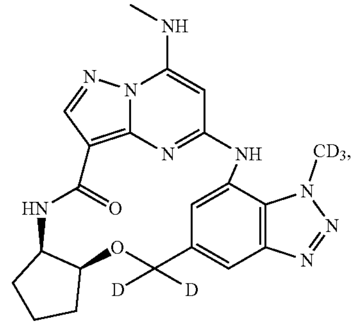
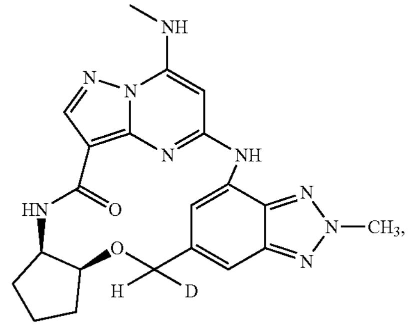
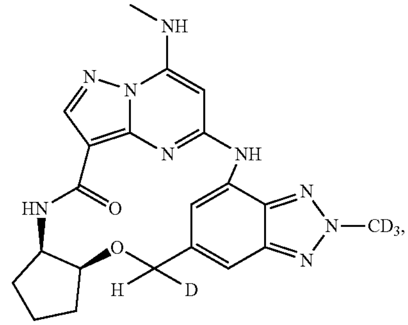
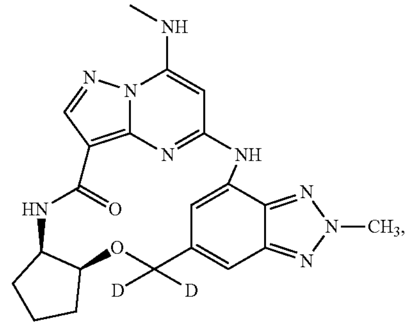

-continued

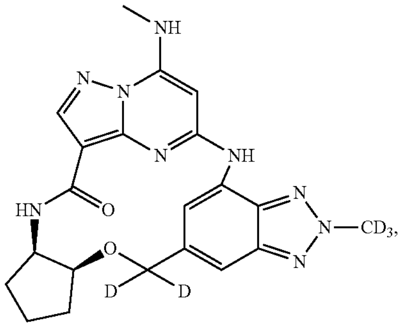

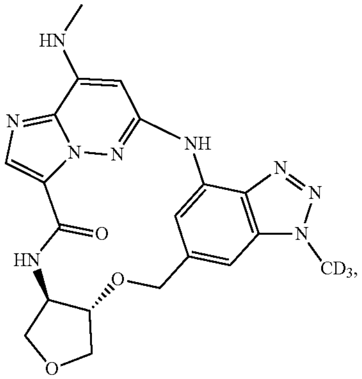

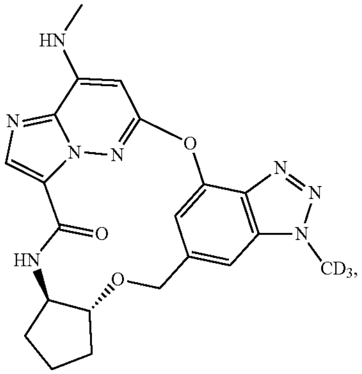

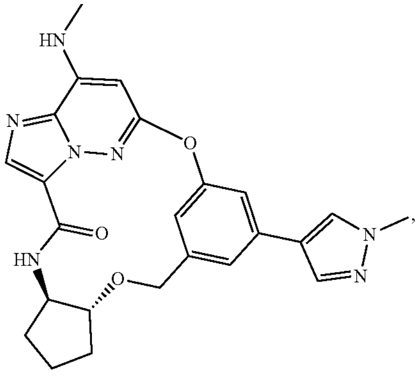

or

-continued

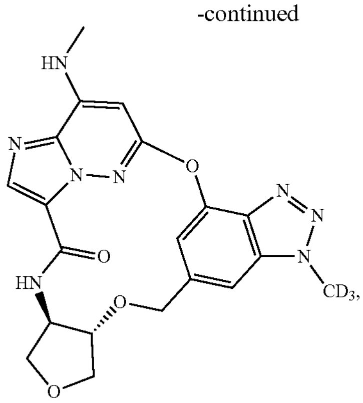

or a pharmaceutically acceptable salt, stereoisomer, or solvate thereof.

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{14}\ alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH, Inc. (Toronto, Canada), Bionet (Cornwall, U.K.), Chem Service Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffian, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line. Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Accordingly, provided herein is a pharmaceutical composition comprising a compound described herein, or a pharmaceutically acceptable salt, solvate, or stereoisomer thereof, and a pharmaceutically acceptable excipient.

In certain embodiments, the compound provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical composition is formulated for oral, topical (including buccal and sublingual), rectal, vaginal, transdermal, parenteral, intrapulmonary, intradermal, intrathecal and epidural and intranasal administration. Parenteral administration includes intramuscular, intravenous, intraarterial, intraperitoneal, or subcutaneous administration. In some embodiments, the pharmaceutical composition is formulated for intravenous injection, oral administration, inhalation, nasal administration, topical administration, or ophthalmic administration. In some embodiments, the pharmaceutical composition is formulated for oral administration. In some embodiments, the pharmaceutical composition is formulated for intravenous injection. In some embodiments, the pharmaceutical composition is formulated as a tablet, a pill, a capsule, a liquid, an inhalant, a nasal spray solution, a suppository, a suspension, a gel, a colloid, a dispersion, a suspension, a solution, an emulsion, an ointment, a lotion, an eye drop, or an ear drop. In some embodiments, the pharmaceutical composition is formulated as a tablet.

Suitable doses and dosage regimens are determined by conventional range-finding techniques known to those of ordinary skill in the art. Generally, treatment is initiated with smaller dosages that are less than the optimum dose of the compound disclosed herein. Thereafter, the dosage is increased by small increments until the optimum effect under the circumstances is reached. In some embodiments, the present method involve the administration of about 0.1 μg to about 50 mg of at least one compound described herein per kg body weight of the subject. For a 70 kg patient, dosages of from about 10 μg to about 200 mg of the compound disclosed herein would be more commonly used, depending on a subject's physiological response.

By way of example only, the dose of the compound described herein for methods of treating a disease as described herein is about 0.001 to about 1 mg/kg body weight of the subject per day, for example, about 0.001 mg, about 0.002 mg, about 0.005 mg, about 0.010 mg, 0.015 mg, about 0.020 mg, about 0.025 mg, about 0.050 mg, about 0.075 mg, about 0.1 mg, about 0.15 mg, about 0.2 mg, about 0.25 mg, about 0.5 mg, about 0.75 mg, or about 1 mg/kg body weight per day. In some embodiments, the dose of compound described herein for the described methods is about 1 to about 1000 mg/kg body weight of the subject being treated per day, for example, about 1 mg, about 2 mg, about 5 mg, about 10 mg, about 15 mg, about 20 mg, about 25 mg, about 50 mg, about 75 mg, about 100 mg, about 150 mg, about 200 mg, about 250 mg, about 500 mg, about 750 mg, or about 1000 mg per day.

Methods of Treatment

The compounds disclosed herein, or pharmaceutically acceptable salts, solvates, or stereoisomers thereof, are useful for the inhibition of kinase activity of one or more enzymes. In some embodiments the kinase inhibited by the compounds and methods is TYK2.

Provided herein are compounds that are inhibitors of TYK2 and are therefore useful for treating one or more disorders associated with activity of TYK2 or mutants thereof.

Provided herein are methods for treating a disease or disorder, wherein the disease or disorder is an autoimmune disorders, inflammatory disorders, proliferative disorders, endocrine disorders, neurological disorders, or disorders associated with transplantation, said method comprising administering to a patient in need thereof, a pharmaceutical composition comprising an effective amount of a compound described herein, or a pharmaceutically acceptable salt, solvate, or stereoisomer thereof.

In some embodiments, the disease or disorder is an autoimmune disorder. In some embodiments the disease or disorder is selected from type 1 diabetes, systemic lupus erythematosus, multiple sclerosis, psoriasis, Behçet's disease, POEMS syndrome, Crohn's disease, ulcerative colitis, and inflammatory bowel disease.

In some embodiments, the disease or disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disease or disorder is a proliferative disorder. In some embodiments, the proliferative disorder is cancer. In some embodiments, the disease or disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disease or disorder is an endocrine disorder. In some embodiments, the endocrine disorder is polycystic ovary syndrome, Crouzon's syndrome, or type 1 diabetes.

In some embodiments, the disease or disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V7311, E957D, and R1027H.

In some embodiments, the disease or disorder is associated with transplantation. In some embodiments the disease or disorder associated with transplantation is transplant rejection, or graft versus host disease.

In some embodiments the disease or disorder is associated with type I interferon, IL-10, IL-12, or IL-23 signaling. In some embodiments the disease or disorder is associated with type I interferon signaling. In some embodiments the disease or disorder is associated with IL-10 signaling. In some embodiments the disorder is associated with IL-12 signaling. In some embodiments the disease or disorder is associated with IL-23 signaling.

Provided herein are methods for treating an inflammatory or allergic condition of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, *Pemphigus vulgaris, Pemphigus foliaceus*, paraneoplastic pemphigus, epidermolysis bullosa acquisita, acne vulgaris, and other inflammatory or allergic conditions of the skin.

Provided herein are methods for treating other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease is acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), or osteoarthritis.

In some embodiments the inflammatory disease is a Th1 or Th17 mediated disease. In some embodiments the Th17 mediated disease is selected from Systemic lupus erythematosus, Multiple sclerosis, and inflammatory bowel disease (including Crohn's disease or ulcerative colitis).

In some embodiments the inflammatory disease is Sjogren's syndrome, allergic disorders, osteoarthritis, conditions of the eye such as ocular allergy, conjunctivitis, keratoconjunctivitis sicca, vernal conjunctivitis, or diseases affecting the nose such as allergic rhinitis.

Combination Therapy

In certain instances, the compound described herein, or a pharmaceutically acceptable salt, solvate, or stereoisomer thereof, is administered in combination with a second therapeutic agent.

In some embodiments, the benefit experienced by a patient is increased by administering one of the compounds described herein with a second therapeutic agent (which also includes a therapeutic regimen) that also has therapeutic benefit.

In one specific embodiment, a compound described herein, or a pharmaceutically acceptable salt, solvate, or stereoisomer thereof, is co-administered with a second therapeutic agent, wherein the compound described herein, or a pharmaceutically acceptable salt, solvate, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt, solvate, or stereoisomer thereof, is initiated prior to, during, or after treatment with a second agent described herein, and continues until any time during treatment with the second agent or after termination of treatment with the second agent. It also includes treatments in which a compound described herein, or a pharmaceutically acceptable salt, solvate, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt, solvate, or stereoisomer thereof, as well as combination therapies, are administered before, during, or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compound of described herein, or a pharmaceutically acceptable salt, solvate, or stereoisomer thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced).

EXAMPLES

Intermediate 1

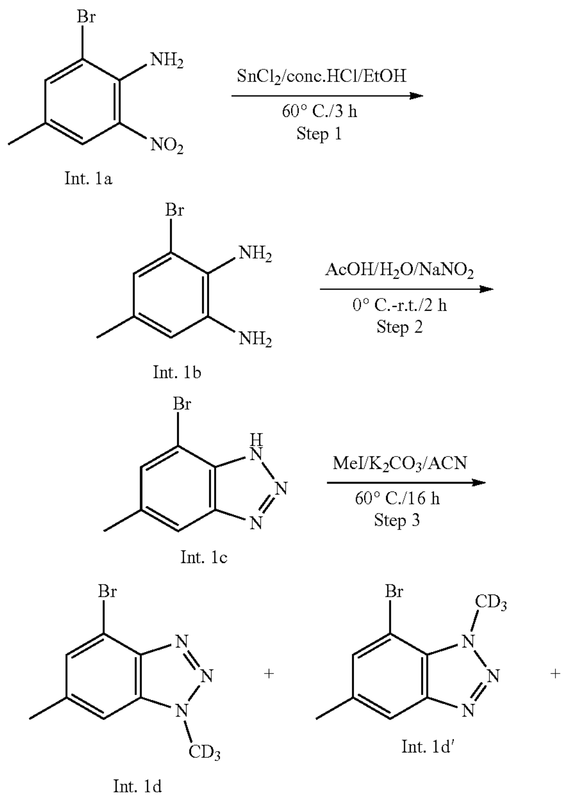

Int. 1a

Int. 1b

Int. 1c

Int. 1d

Int. 1d′

-continued

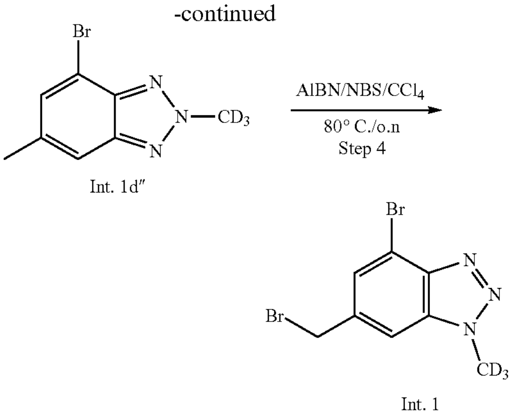

Int. 1d″

Int. 1

Step 1: Intermediate 1b

To a solution of Intermediate 1a (84 g, 363.6 mmol) in EtOH (464 mL) and conc. HCl (116 mL) was added $SnCl_2$ (408 g, 2.16 mol). The reaction mixture was stirred at 60° C. for 3 h under $N_2$. After cooled to room temperature, the mixture was poured into 2M NaOH aqueous solution (750 mL) to pH=12 at 0° C. DCM (800 mL) was added to the mixture, and the white solid was removed by filtration. The organic layer was separated, and the aqueous phase was extracted with DCM (500 mL*2). The combined organic extracts were washed with brine, dried over $Na_2SO_4$, and concentrated. The crude was purified by silica gel flash column chromatography (Petroleum Ether/EtOAc=2/1) to afford the product Intermediate 1b (49 g, 67% yield) as a yellow solid. LCMS $[M+1]^+$=201.2.

Step 2: Intermediate 1c

A solution of Intermediate 1b (49 g, 243.8 mmol) in AcOH (530 mL) and $H_2O$ (100 mL) was cooled to 0° C., followed by the addition of $NaNO_2$ (13.36 g, 193.6 mmol) in water (167 mL). The reaction mixture was stirred for 30 min at r.t. After completion, a gradual formation of a yellow precipitate was observed. The solid was collected by filtration and washed with 65% AcOH in water, concentrated to afford the product Intermediate 1c (40.7 g, 78% yield) as a yellow solid. LCMS $[M+1]^+$=212.2.

Step 3: Intermediate 1d, Intermediate 1d', and Intermediate 1d"

To a solution of Intermediate 1c (2.0 g, 9.48 mmol) in THF (13 mL) were added NaH (545 mg, 14.2 mmol) and $CD_3I$ (2.75 g, 18.96 mmol). The reaction mixture was stirred at 0° C. to r.t. for 16 h. After cooled to room temperature, the solid was filtered off and the filtrate was concentrated. The crude product was purified by silica gel flash column chromatography (Petroleum Ether/DCM=1/1) to afford the product Intermediate id (800 mg, 24% yield, retention time: 1.48 min) as a white solid, Intermediate 1d' (400 mg, 18% yield, retention time: 1.42 min) as a white solid, and Intermediate 1d" (500 mg, 25% yield, retention time: 1.33 min) as a white solid. LCMS $[M+1]^+$=229.2.

Step 4: Intermediate 1

To a solution of Intermediate id (800 mg, 3.5 mmol) in $CCl_4$ (10 mL) was added NBS (935 mg, 5.25 mmol) and AIBN (287 mg, 1.75 mmol). The reaction mixture was stirred at 80° C. overnight. After cooled to room temperature, the solvent was removed, and the residue was purified by silica gel flash column chromatography (Petroleum Ether/DCM=1/1) to afford the product Intermediate 1 (700 mg, 65% yield) as a white solid. LCMS $[M+1]^+=306.2$.

Example 1: General Procedure for Synthesis of Example 1

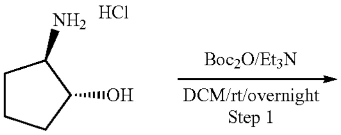

Example 1a

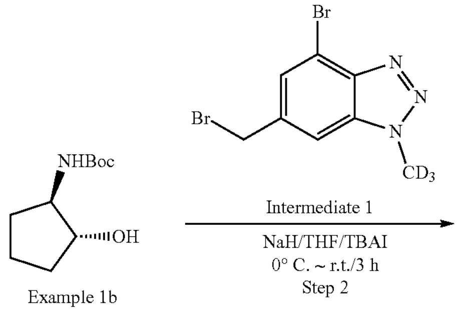

Example 1b

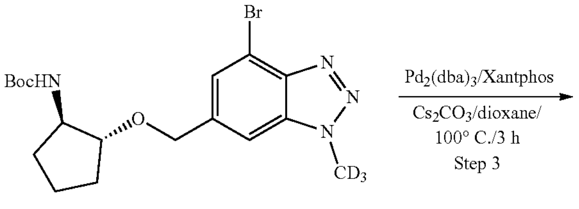

Example 1d

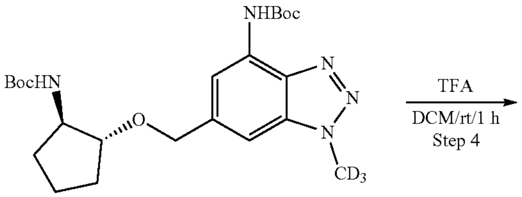

Example 1e

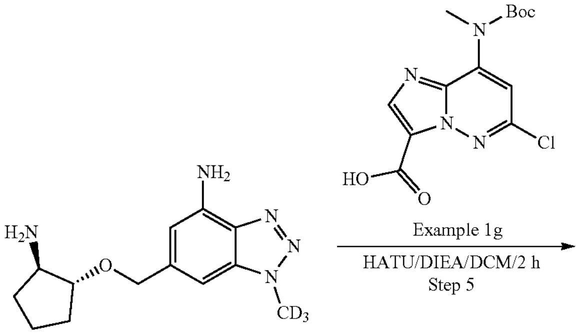

Example 1f

-continued

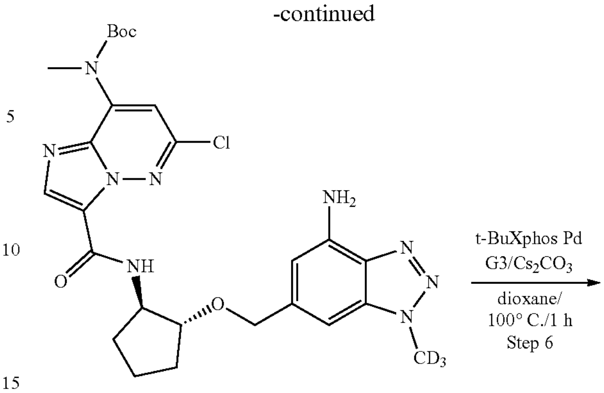

Example 1h

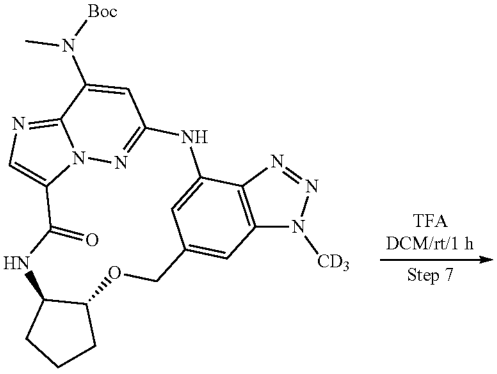

Example 1i

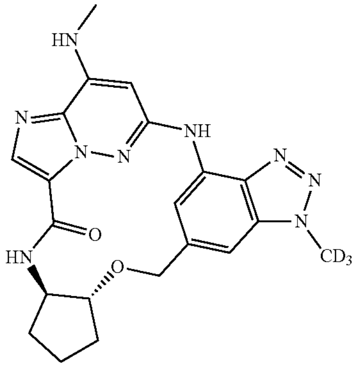

Example 1

Step 1: Example 1b

To a solution of Example 1a (5.0 g, 36.34 mmol) and $Et_3N$ (5.52 g, 54.50 mmol) in DCM (100 mL) was added $Boc_2O$ (9.52 g, 43.60 mmol) at 0° C. The reaction was allowed to warm to room temperature and stirred overnight. The reaction mixture was concentrated and the crude product was purified by column chromatography eluting with DCM: MeOH (3%~5%) to give Example 1b (5.0 g, yield 68%) as a white solid. LCMS $[M\text{-}Boc+1]^+=102.1$.

Step 2: Example 1d

To a solution of Example 1b (300 mg, 1.49 mmol) in THF (3 mL) were added Intermediate 1 (459 mg, 1.49 mmol), TBAI (55 mg, 0.149 mmol) and NaH (72 mg, 1.79 mmol) at 0° C. The resulting mixture was stirred at room temperature for 3 h. $H_2O$ (100 mL) was added, and the mixture was extracted with EtOAc (30 mL*3). The combined organic layers were washed with brine (30 mL*3), dried over anhydrous sodium sulfate, filtered and concentrated under reduced pressure. The residue was purified by column chromatography eluting with Petroleum Ether/EtOAc (60/40) to give Example 1d (0.3 g, yield 92%) as yellow oil. LCMS $[M-2Boc+1]^+$=328.1.

Step 3: Example 1e

To a solution of Example 1d (0.3 g, 0.72 mmol) in dioxane (3 mL) was added $Pd_2(dba)_3$ (66 mg, 0.0723 mmol), Xant-Phos (84 mg, 0.14 mmol), $Cs_2CO_3$ (707 mg, 2.17 mmol), and $NH_2Boc$ (127 mg, 1.09 mmol). The reaction mixture was degassed with argon for three times and stirred at 100° C. for 3 h. The reaction mixture was poured into water (100 mL). The mixture was extracted with DCM (50 mL*3). The combined organic layers were washed with brine (50 mL*3), dried over anhydrous sodium sulfate, filtered and concentrated under reduced pressure. The residue was purified by column chromatography eluting with MeOH/DCM (5%~10%) to give Example 1e (0.3 g, yield 47%) as colorless oil. LCMS $[M-Boc+1]^+$=265.2.

Step 4: Example 1f

To a solution of Example 1e (0.3 g, 0.645 mmol) in DCM (5 mL) was added TFA (2.58 g, 22.60 mmol) at room temperature. The resulting solution was stirred at room temperature for 1 h. The mixture was concentrated in vacuum. The residue was adjusted pH to 9 with 1 M $NaHCO_3$. After that, the mixture was extracted with DCM (50 mL*3). The combined organic layers were washed with brine (50 mL*3), dried over anhydrous sodium sulfate, filtered and concentrated. The solvent was removed in vacuum. The residue Example 1f (0.17 g, yield 100%) was obtained as yellow oil, which was used to next step without further purification. LCMS $[M-Boc+1]^+$=265.2.

Step 5: Example 1h

To a solution of Example 1f (0.16 g, 0.61 mmol) in DCM (6 mL) were added DIEA (469 mg, 3.63 mmol), Example 1g (198 mg, 0.61 mmol) and HATU (230 mg, 0.61 mmol). The reaction mixture was stirred at room temperature for 1 h. Water (30 mL) was added, and the mixture was extracted with DCM (10 mL*3). The combined organic layers were washed with brine (10 mL*3), dried over anhydrous sodium sulfate, filtered and concentrated. The residue was purified by column chromatography eluting with MeOH/DCM (7%) to give Example 1h (0.11 g, yield 11%) as a colorless solid. LCMS $[M+1]^+$=573.2.

Step 6: Example 1i

To a solution of Example 1h (0.1 g, 0.17 mmol) in dioxane (1 mL) was added t-BuXphosPd G3 (28 mg, 0.035 mmol) and $Cs_2CO_3$ (171 mg, 0.52 mmol). The reaction mixture was degassed with argon for three times and stirred at 100° C. for 75 min. Water (50 mL) was added, and the mixture was extracted with DCM (30 mL*3). The combined organic layers were washed with brine (30 mL*3), dried over anhydrous sodium sulfate, filtered and concentrated. The residue was purified by column chromatography eluting with MeOH/DCM (6%) to give Example 1i (0.1 g, yield: quant.) as a yellow solid. LCMS $[M+1]^+$=537.3.

Step 7: Example 1

To a solution of Example 1i (0.1 g, 0.19 mmol) in DCM (1 mL) was added TFA (531 mg, 4.66 mmol) at room temperature. The resulting solution was stirred at room temperature for 2 h. The mixture was concentrated under reduced pressure. The residue was adjusted pH to 9 with 1 M $NaHCO_3$. After that, the mixture was extracted with DCM (50 mL*3). The combined organic layers were washed with brine (50 mL*3), dried over anhydrous sodium sulfate, filtered and concentrated. The residue was purified by Pre-TLC (MeOH/DCM=10%) to give Example 1 (3.1 mg, yield 3.8%) as a white solid. LCMS $[M+1]^+$=437.3. $^1H$ NMR (400 MHz, DMSO-$d_6$) δ 9.94 (s, 1H), 9.20 (d, J=4.6 Hz, 1H), 8.14 (s, 1H), 7.84 (d, J=1.8 Hz, 1H), 7.57 (d, J=5.2 Hz, 1H), 7.30 (s, 1H), 6.40 (s, 1H), 4.94 (d, J=14.6 Hz, 1H), 4.60 (d, J=14.5 Hz, 1H), 3.83 (s, 1H), 3.73 (t, J=8.4 Hz, 1H), 2.91 (d, J=4.8 Hz, 3H), 2.27 (d, J=10.3 Hz, 1H), 2.14-1.93 (m, 2H), 1.72 (d, J=10.6 Hz, 1H), 1.61-1.42 (m, 2H).

Example A. TYK2 JH2 Domain Binding Assay

Binding constants for the compounds described herein against the JH2 domain were determined by the following protocol for a KINOMEscan® assay (DiscoveRx). A fusion protein of a partial length construct of human TYK2 (JH2domain-pseudokinase) (amino acids G556 to D888 based on reference sequence NP_003322.3) and the DNA binding domain of NFkB is expressed in transiently transfected HEK293 cells. From these HEK 293 cells, extracts are prepared in M-PER extraction buffer (Pierce) in the presence of Protease Inhibitor Cocktail Complete (Roche) and Phosphatase Inhibitor Cocktail Set II (Merck) per manufacturers' instructions. The TYK2 (JH2domain-pseudokinase) fusion protein is labeled with a chimeric double-stranded DNA tag containing the NFkB binding site fused to an amplicon for qPCR readout, which is added directly to the expression extract (the final concentration of DNA-tag in the binding reaction is 0.1 nM).

Streptavidin-coated magnetic beads (Dynal M280) are treated with a biotinylated small molecule ligand for 30 minutes at room temperature to generate affinity resins the binding assays. The liganded beads are blocked with excess biotin and washed with blocking buffer (SeaBlock (Pierce), 1% BSA, 0.05% Tween 20, 1 mM DTT) to remove unbound ligand and to reduce nonspecific binding.

The binding reaction is assembled by combining 16 μl of DNA-tagged kinase extract, 3.8 μl liganded affinity beads, and 0.18 μl test compound (PBS/0.05% Tween 20/10 mM DTT/0.1% BSA/2 μg/ml sonicated salmon sperm DNA)]. Extracts are used directly in binding assays without any enzyme purification steps at a ≥10,000-fold overall stock dilution (final DNA-tagged enzyme concentration <0.1 nM). Extracts are loaded with DNA-tag and diluted into the binding reaction in a two-step process. First extracts are diluted 1:100 in 1× binding buffer (PBS/0.05% Tween 20/10 mM DTT/0.1% BSA/2 μg/ml sonicated salmon sperm DNA) containing 10 nM DNA-tag. This dilution is allowed to equilibrate at room temperature for 15 minutes and then subsequently diluted 1:100 in 1× binding buffer. Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds are then diluted directly into the assays such that the final concentration of DMSO was 0.9%. All reactions are performed in polypropylene 384-well plates. Each was a final volume of 0.02 mL. Assays are incubated with shaking for 1 hour at room temperature. Then the beads are pelleted and washed with wash buffer (1×PBS, 0.05% Tween 20) to remove displaced kinase and test compound. The washed based are re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. qPCR reactions are assembled by adding 2.5 μL of kinase eluate to 7.5 μL of qPCR master mix containing 0.15 μM amplicon primers and 0.15 μM amplicon probe. The qPCR protocol consisted of a 10 minute hot start at 95° C., followed by 35 cycles of 95° C. for 15 seconds, 60° C. for 1 minute.

Test compounds are prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds are then diluted directly into the assays such that the final concentration of DMSO was 0.9%. The Kds are determined using a compound top concentration of 30,000 nM. Kd measurements are performed in duplicate.

Binding constants (Kds) were calculated with a standard dose-response curve using the Hill equation:

$$\text{Response} = \text{Background} + \frac{(\text{Signal} - \text{Background})}{\left(1 + \left(\frac{Kd^{Hill\ Slope}}{\text{Dose}^{Hill\ Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, Q. Appl. Math. 2, 164-168 (1944)).

The results are shown in table 1.

TABLE 1

| Ex. | TYK2 (JH2 domain) binding Kd (nM) |
|---|---|
| 1 | 0.0022 |

Example B: INFα Induced pSTAT5 in Human PBMC

Fresh Human PBMCs were resuspended in RPMI 1640 medium with 10% FBS. Cells were seeded in a round bottom 96-well plate at the concentration of 200,000 cells/well. A 10-point dilution series of test compound (top dose 10 uM, 1:5 dilution) was added to the well using the liquid dispenser (Tecan D300e) and incubated for 1 hour at 37 C. Then human INFα recombinant protein (R&D Systems) was added to the well at the final concentration of 5000 units/ml and incubated for 15 minutes at 37 C. Cell lysates were prepared and analyzed by Phospho STAT5 (Tyr693) Kit (Meso Scale Discovery) following manufacturer's protocol.

For calculation of the inhibition rate, the relative pSTAT5 signal of each well=pSTAT5 signal of each well−the average pSTAT5 signal of baseline.

The inhibition %=(the average pSTAT5 signal of INFα treatment wells−the relative of pSTAT5 signal in each compound containing well)/the average pSTAT5 signal of INFα treatment wells*100%

The curve was plotted as the inhibition % (y-axis) vs. compounds concentration (x-axis) and was fitted with log (inhibitor) vs. normalized response—Variable slope by GraphPad Prism7.0. Control is BMS-986165:

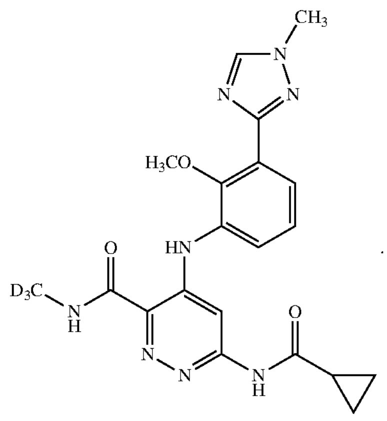 [SMILES: [2H]C([2H])([2H])NC(=O)c1nnc(NC(=O)C2CC2)cc1Nc1cccc(-c2ncn(C)n2)c1OC]

The results are shown in table 2.

TABLE 2

| Ex. | p-STAT5 $IC_{50}$ (nM) | Relative $IC_{50}$ to control |
|---|---|---|
| 1 | 1.7 | 1.1 |

Example C: Pharmaceutical Compositions

Example C1: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example C2: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example C3: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

The examples and embodiments described herein are for illustrative purposes only and in some embodiments, various modifications or changes are to be included within the purview of disclosure and scope of the appended claims.

What is claimed is:

1. A compound of Formula (Ia) or Formula (If), or a pharmaceutically acceptable salt, or stereoisomer thereof:

Formula (Ia)

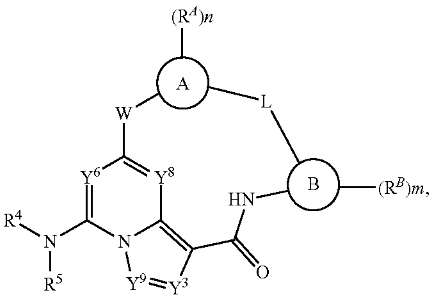

Formula (If)

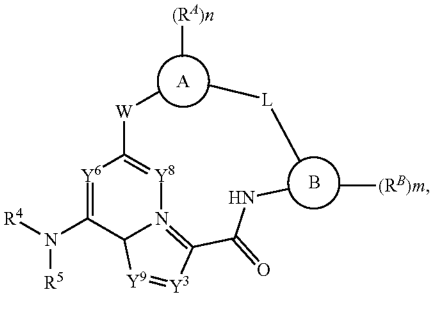

wherein:

L is a $C_1$-$C_4$alkylene; wherein one or two carbon atoms are optionally replaced by a heteroatom selected from oxygen, sulfur, and nitrogen; and wherein L is optionally substituted with one or more $R^L$;

$R^L$ is independently selected for each occurrence from the group consisting of deuterium, halogen, —CN, —$OR^b$, —$NO_2$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl;

or two $R^L$ on the same carbon are taken together to form an oxo, a cycloalkyl, or a heterocycloalkyl;

Ring A is a bicyclic heteroaryl or phenyl;

Ring B is a 5-6 membered cycloalkyl or a 5-6 membered heterocycloalkyl;

$R^A$ is independently selected for each occurrence from the group consisting of deuterium, halogen, $C_1$-$C_6$alkyl, $C_1$-$C_6$haloalkyl, $C_1$-$C_6$deuteroalkyl, aryl, and heteroaryl; wherein each alkyl, aryl, and heteroaryl is independently optionally substituted with one or more $R^{A1}$;

$R^{A1}$ is independently selected for each occurrence from the group consisting of deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^b$C(=O)$NR^cR^d$, —$NR^b$C(=O)$R^a$, —$NR^b$C(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl;

n is 1 or 2;

each $R^B$ is independently selected for each occurrence from the group consisting of deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^b$C(=O)$NR^cR^d$, —$NR^b$C(=O)$R^a$, —$NR^b$C(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl; wherein each alkyl, alkenyl, alkynyl, cycloalkyl, heterocycloalkyl, aryl, and heteroaryl is independently optionally substituted with one or more $R^{B1}$;

or two $R^B$ on the same carbon are taken together to form an oxo;

$R^{B1}$ is independently selected for each occurrence from the group consisting of deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^b$C(=O)$NR^cR^d$, —$NR^b$C(=O)$R^a$, —$NR^b$C(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl;

m is 0-4;

$Y^3$ is $CR^3$;

$Y^6$ is $CR^6$;

$Y^8$ is N;

$Y^9$ is N;

$R^3$ and $R^6$ are independently selected from the group consisting of hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^b$C(=O)$NR^cR^d$, —$NR^b$C(=O)$R^a$, —$NR^b$C(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, and $C_2$-$C_6$alkynyl;

$R^4$ is selected from the group consisting of hydrogen, $C_1$-$C_6$alkyl, $C_1$-$C_6$heteroalkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl; wherein each alkyl, alkenyl, alkynyl, cycloalkyl, heterocycloalkyl, aryl, and heteroaryl are optionally substituted with one or more $R^{4a}$;

$R^{4a}$ is independently selected for each occurrence from the group consisting of deuterium, halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, and heteroaryl;

or two $R^{4a}$ on the same carbon are taken together to form an oxo;

$R^5$ is selected from the group consisting of hydrogen, $C_1$-$C_6$alkyl, $C_1$-$C_6$haloalkyl, and $C_1$-$C_6$deuteroalkyl;

W is —O— or —$NR^7$—;

$R^7$ is selected from the group consisting of hydrogen, $C_1$-$C_6$alkyl, $C_1$-$C_6$haloalkyl, and $C_1$-$C_6$deuteroalkyl;

$R^a$ is independently selected for each occurrence from the group consisting of $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl;

$R^b$ is independently selected for each occurrence from the group consisting of hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl; and $R^c$ and $R^d$ are independently selected for each occurrence from the group consisting of hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, and heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —$NH_2$, —C(═O)Me, —C(═O)OH, —C(═O)OMe, $C_1$-$C_6$alkyl, or $C_1$-$C_6$haloalkyl.

2. The compound of claim 1, or a pharmaceutically acceptable salt or stereoisomer thereof, wherein:

Ring A is selected from the group consisting of indolyl, indazolyl, benzimidazolyl, benzotriazolyl, benzothiophenyl, benzothiazolyl, benzofuranyl, and benzoxazolyl.

3. The compound of claim 1, or a pharmaceutically acceptable salt or stereoisomer thereof, wherein:

$R^6$ is hydrogen.

4. The compound of claim 1, or a pharmaceutically acceptable salt or stereoisomer thereof, wherein:

$R^3$ is hydrogen.

5. The compound of claim 1, or a pharmaceutically acceptable salt or stereoisomer thereof, wherein:

$R^4$ is hydrogen, $C_1$-$C_6$alkyl, $C_1$-$C_6$haloalkyl, or $C_1$-$C_6$deuteroalkyl.

6. The compound of claim 1, or a pharmaceutically acceptable salt or stereoisomer thereof, wherein:

$R^4$ is $C_1$-$C_6$alkyl or $C_1$-$C_6$deuteroalkyl.

7. The compound of claim 1, or a pharmaceutically acceptable salt or stereoisomer thereof, wherein:

$R^5$ is hydrogen.

8. The compound of claim 1, or a pharmaceutically acceptable salt or stereoisomer thereof, wherein:

$R^7$ is hydrogen or $C_1$-$C_6$alkyl.

9. The compound of claim 1, or a pharmaceutically acceptable salt or stereoisomer thereof, wherein:

each $R^A$ is independently $C_1$-$C_6$alkyl, $C_1$-$C_6$haloalkyl, or $C_1$-$C_6$deuteroalkyl.

10. The compound of claim 1, or a pharmaceutically acceptable salt or stereoisomer thereof, wherein:

each $R^A$ is independently $C_1$-$C_6$deuteroalkyl.

11. The compound of claim 1, or a pharmaceutically acceptable salt or stereoisomer thereof, wherein:

L is a $C_2$-$C_4$alkylene; wherein one carbon atom is optionally replaced by a heteroatom selected from oxygen, sulfur, and nitrogen; and wherein L is optionally substituted with one or more $R^L$.

12. The compound of claim 1, or a pharmaceutically acceptable salt or stereoisomer thereof, wherein:

L is a $C_2$-$C_3$alkylene; wherein one carbon atom is optionally replaced by a heteroatom selected from oxygen, sulfur, and nitrogen; and wherein L is optionally substituted with one or more $R^L$.

13. The compound of claim 1, or a pharmaceutically acceptable salt or stereoisomer thereof, wherein:

L is a $C_2$-alkylene; wherein one carbon atom is optionally replaced by a heteroatom selected from oxygen, sulfur, and nitrogen; and wherein L is optionally substituted with one or more $R^L$.

14. The compound of claim 11, or a pharmaceutically acceptable salt or stereoisomer thereof, wherein:

the heteroatom is an oxygen or a sulfur.

15. The compound of claim 1, or a pharmaceutically acceptable salt or stereoisomer thereof, wherein:

L is —$CH_2$—O— or —O—$CH_2$—.

16. A compound selected from the group consisting of:

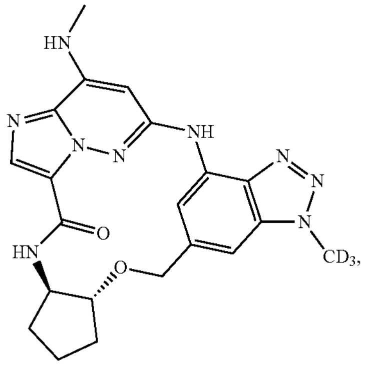

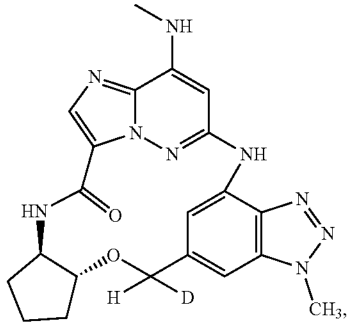

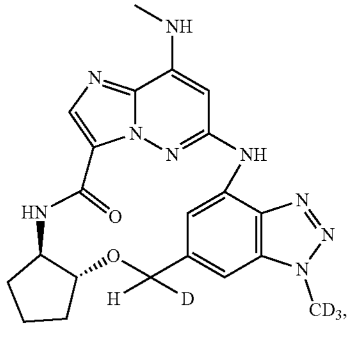

-continued
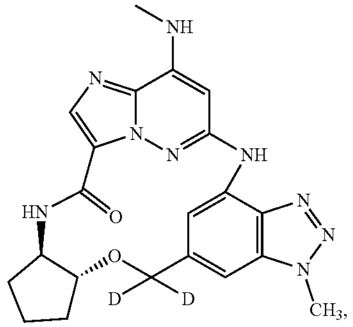
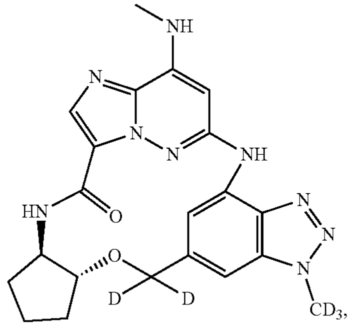
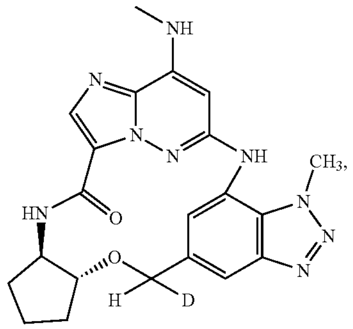
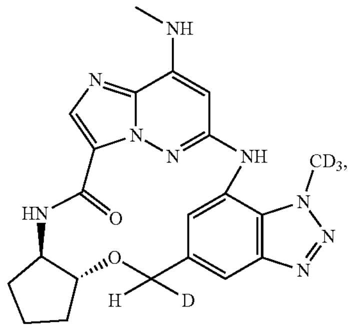
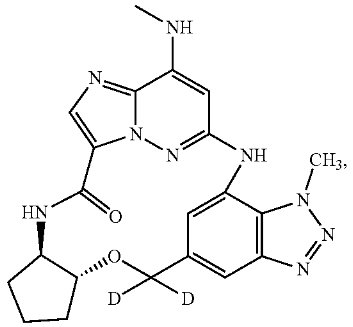
-continued
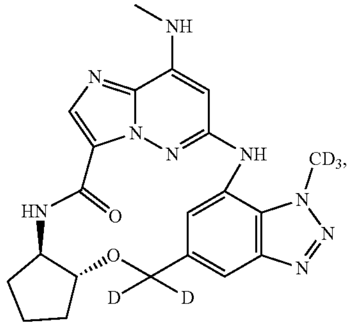
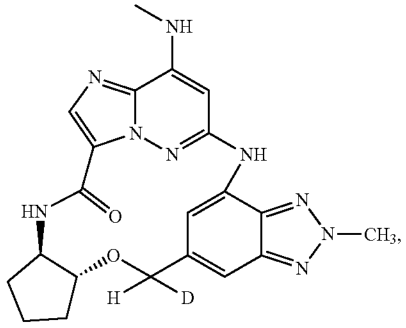
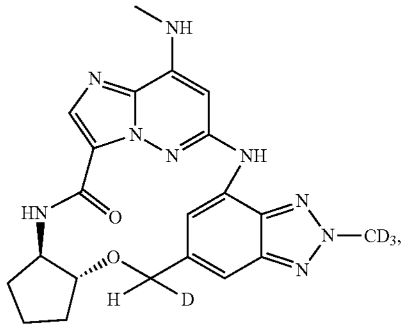
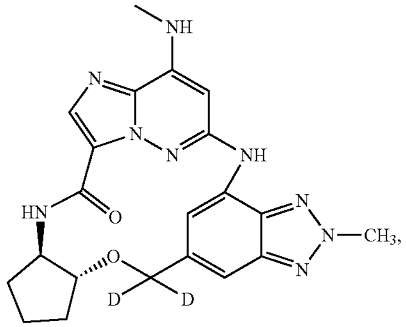
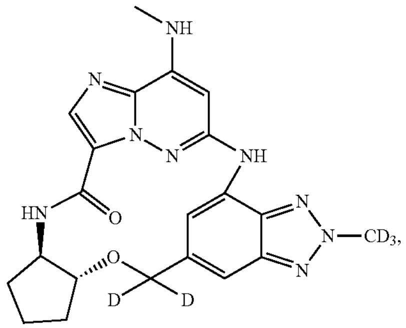

-continued
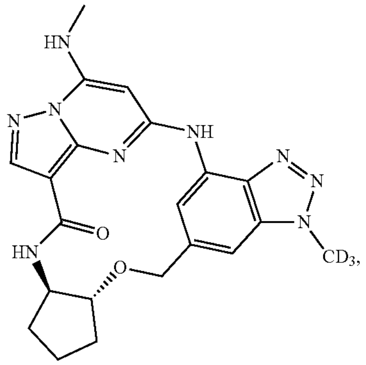
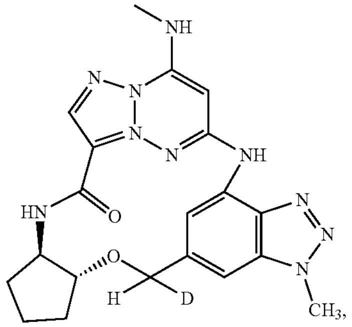
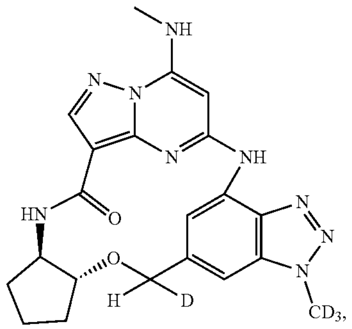
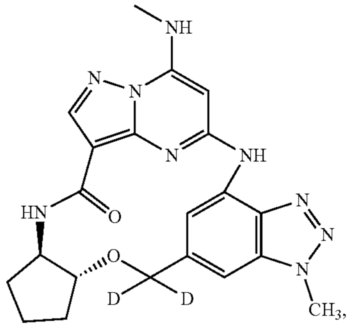
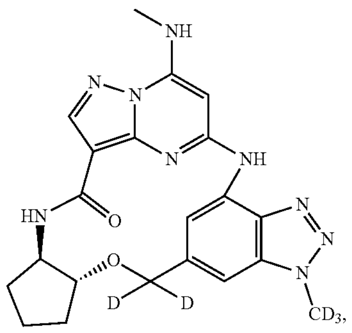
-continued
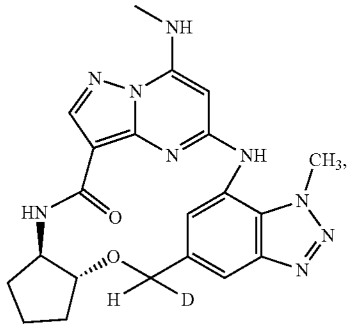
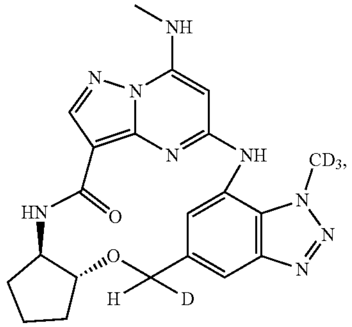
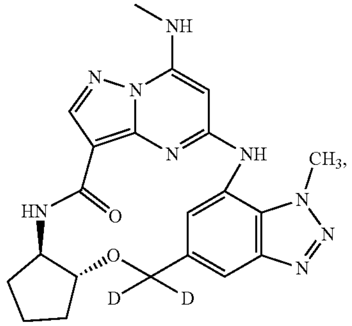
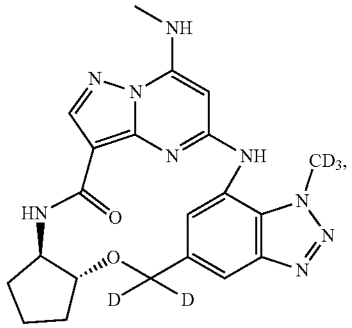
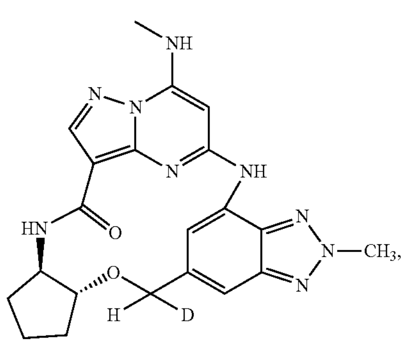

-continued
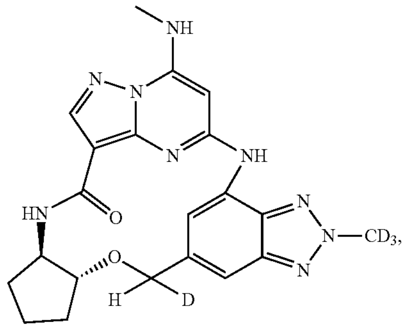
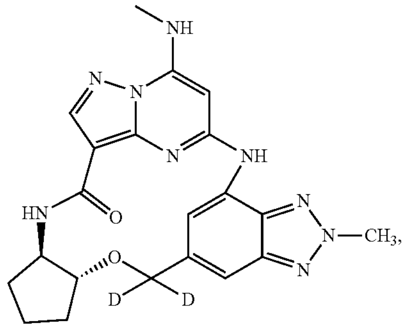
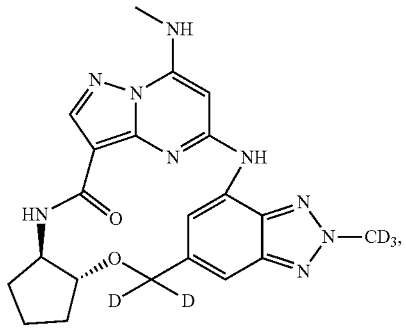
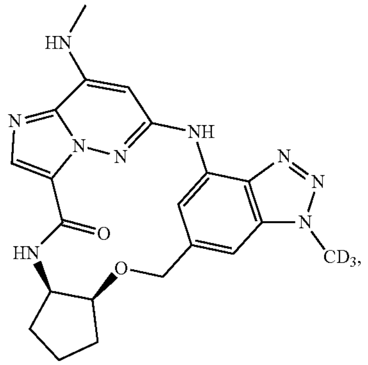
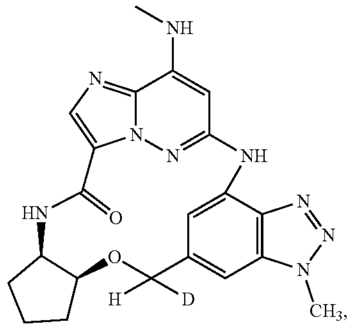
-continued
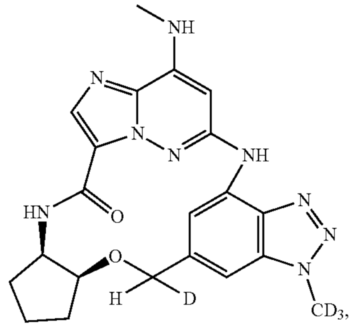
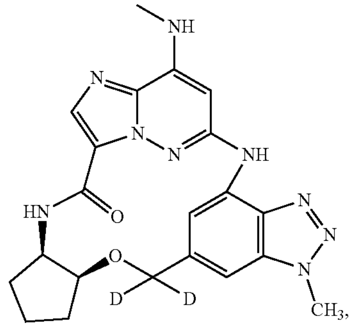
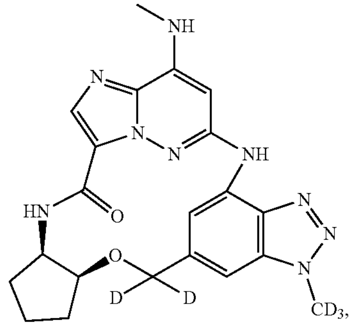
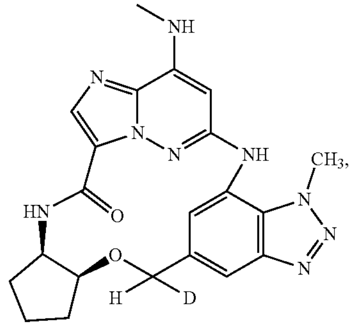
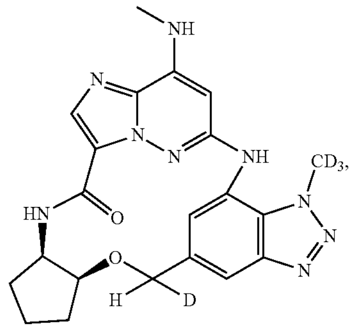

-continued
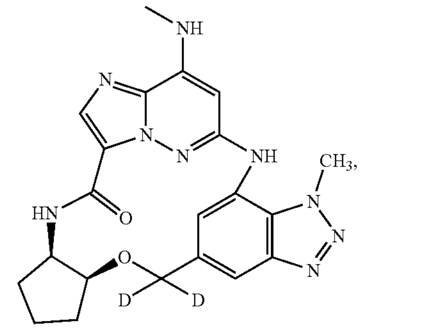
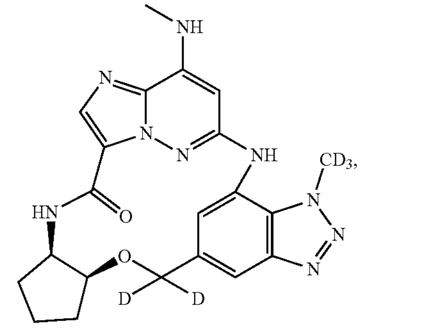
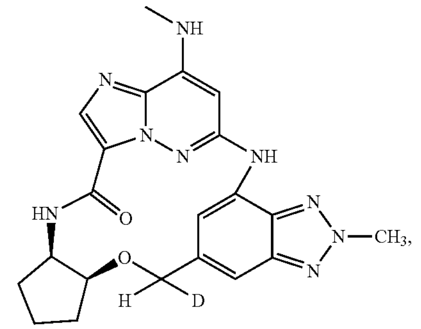
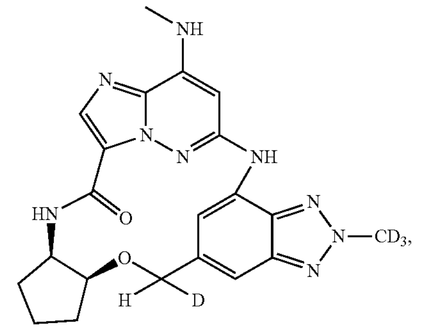
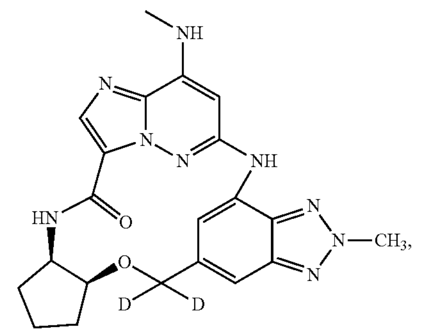
-continued
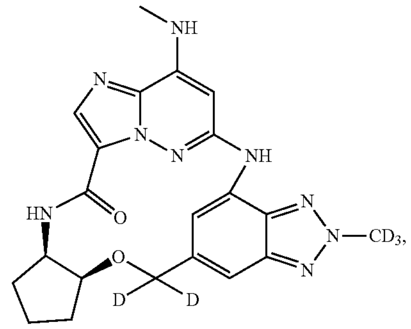
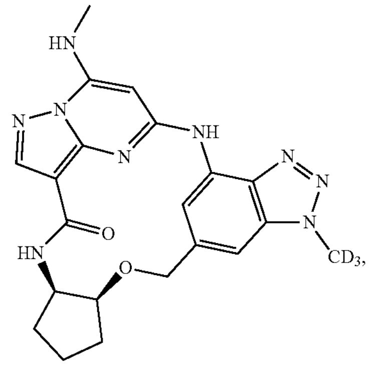
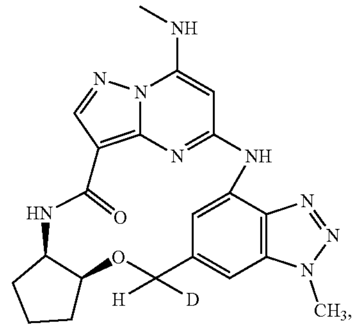
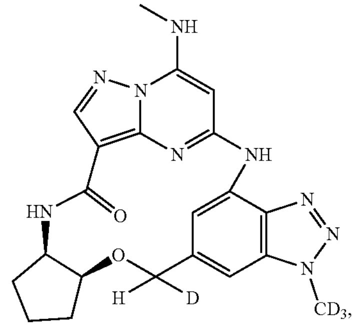
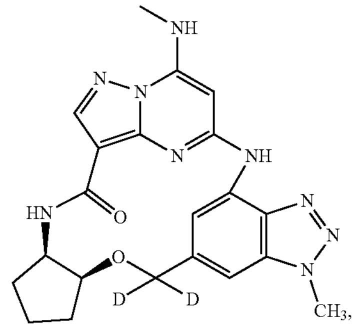

-continued
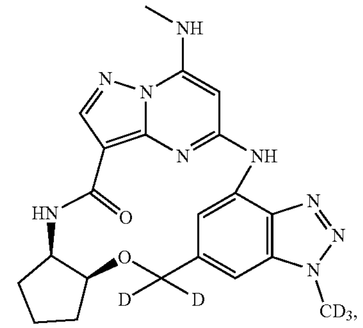
,
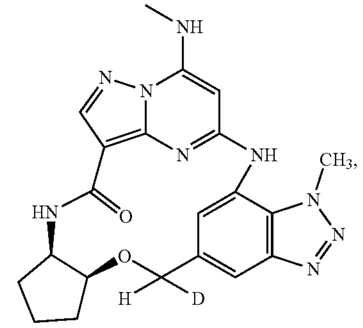
,
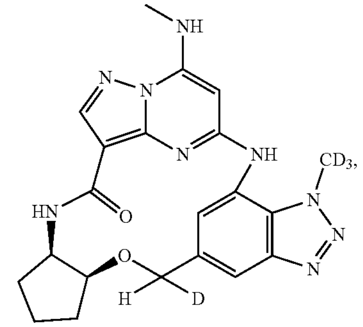
,
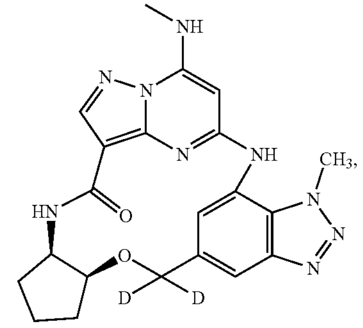
,
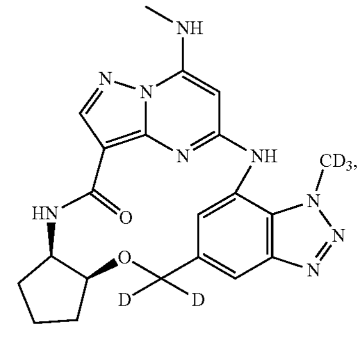
,
-continued
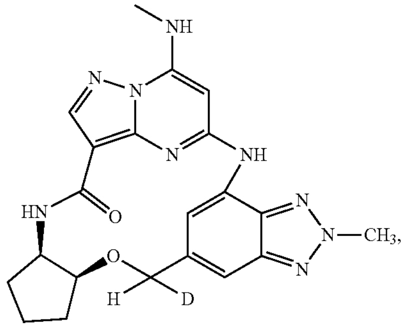
,
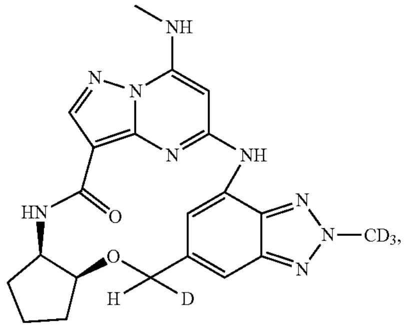
,
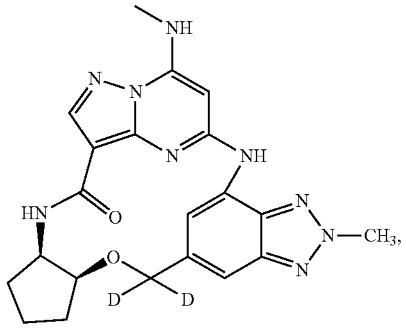
,
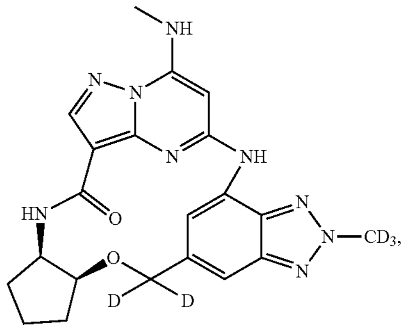
,
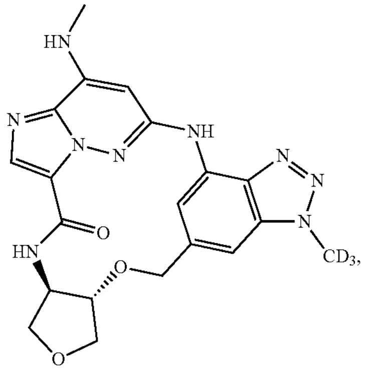
, -continued
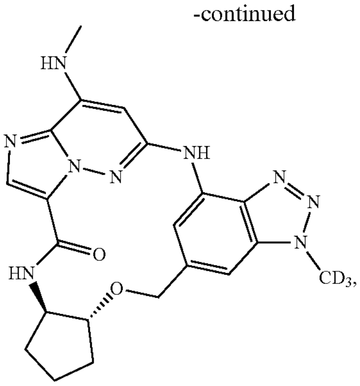
,
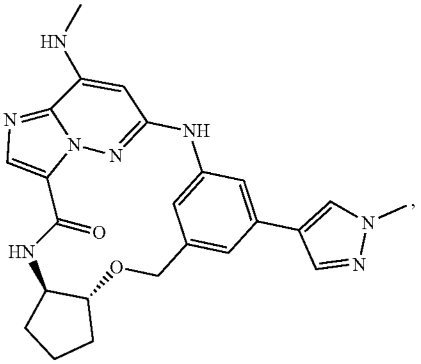
, and
-continued
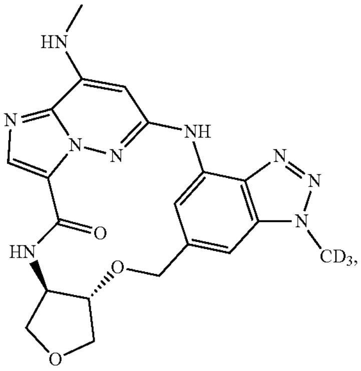 [SMILES: [2H]C([2H])([2H])n1nnc2c3cc(cc21)CO[C@@H]1COC[C@H]1NC(=O)c1cnc2c(NC)cc(nn12)N3]
,
or a pharmaceutically acceptable salt or stereoisomer thereof.
17. A pharmaceutical composition comprising a therapeutically effective amount of the compound of claim 1, or a pharmaceutically acceptable salt or stereoisomer thereof, and a pharmaceutically acceptable excipient.
* * * * *